United States Patent [19]

Furutachi et al.

[11] Patent Number: 4,822,730
[45] Date of Patent: Apr. 18, 1989

[54] SILVER HALIDE COLOR PHOTOGRAPHIC LIGHT-SENSITIVE MATERIALS CONTAINING A PYRAZOLOAZOLE MAGENTA COUPLER

[75] Inventors: Nobuo Furutachi; Toshio Kawagishi; Kiyoshi Nakazyo, all of Kanagawa, Japan

[73] Assignee: Fuji Photo Film Co., Ltd., Kanagawa, Japan

[21] Appl. No.: 56,312

[22] Filed: May 28, 1987

Related U.S. Application Data

[63] Continuation of Ser. No. 773,162, Sep. 6, 1985, abandoned.

[30] Foreign Application Priority Data

Sep. 6, 1984 [JP] Japan .................. 59-187204
Dec. 20, 1984 [JP] Japan .................. 59-268924

[51] Int. Cl.$^4$ .................. C03C 1/08; C03C 7/26; C03C 7/32
[52] U.S. Cl. .................. 430/558; 430/554; 430/555
[58] Field of Search .................. 430/558, 554, 555

[56] References Cited

U.S. PATENT DOCUMENTS

| | | | |
|---|---|---|---|
| 4,500,630 | 2/1985 | Sato et al. | 430/372 X |
| 4,522,916 | 7/1985 | Hirano | 430/558 X |
| 4,524,132 | 7/1985 | Aoki et al. | 430/552 |
| 4,540,654 | 9/1985 | Sato et al. | 430/558 X |
| 4,543,323 | 9/1985 | Iijima et al. | 430/558 X |

Primary Examiner—Mukund J. Shah
Attorney, Agent, or Firm—Sughrue, Mion, Zinn, Macpeak, and Seas

[57] ABSTRACT

A silver halide color photographic material comprising a support having formed thereon at least one silver halide emulsion layer containing a pyrazoloazole series magenta coupler having at least one group expressed by the formula [S] below at a position other than the coupling active position.

$$-(A)_n-L-B \qquad [S]$$

wherein A represents a substituted or unsubstituted alkylene group, a substituted or unsubstituted cycloalkylene group, a substituted or unsubstituted arylene group, or a substituted or unsubstituted aralkylene group, in which in the main chain of said alkylene group, cycloalkylene group, arylene group, or aralkylene group, $-O-$, $-S-$, $-CO-$, $-CO_2-$, $-OCO-$,

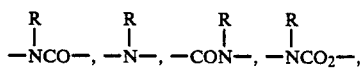

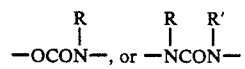

may be contained; L represents

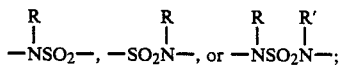

B represents a hydrogen atom or a substituted or unsubstituted alkyl or aryl group which does not contain therein $-SO_2-$; n is 0 or 1; and R and R' each represents a hydrogen atom, a substituted or unsubstituted alkyl group, or a substituted or unsubstituted aryl group. In the above, in the case that the pyrazoloazole series magenta coupler is a 1H-pyrazolo[5,1-c][1,2,4]triazole derivative, A does not represent an aralkylene group containing an arylene group directly connected to L. The silver halide color photographic light-sensitive material has improved coloring properties.

8 Claims, No Drawings

SILVER HALIDE COLOR PHOTOGRAPHIC LIGHT-SENSITIVE MATERIALS CONTAINING A PYRAZOLOAZOLE MAGENTA COUPLER

This is a continuation of application Ser. No. 773,162, filed Sept. 6, 1985, now abandoned.

FIELD OF THE INVENTION

This invention relates to a silver halide color photographic material and, more particularly to a silver halide color photographic material having improved coloring properties. More specifically, the invention relates to a silver halide color photographic material containing a pyrazoloazole series magenta coupler having at least one group expressed by the formula [S] below at a position other than the coupling active position.

$$-(A)_n-L-B \qquad [S]$$

wherein A, L, B, and n are defined hereinafter.

BACKGROUND OF THE INVENTION

For silver halide color photographic materials, light-sensitive silver halide emulsions and so-called dye-forming couplers forming dyes by undergoing a reaction with the oxidation product of an aromatic primary amine developing agent are frequently used and it is well-known to use a combination of a yellow coupler, a cyan coupler and a magenta coupler as such dye-forming couplers.

In these couplers, a 5-pyrazolone series coupler which is frequently used as a magenta coupler presents serious problems for color reproduction such as the azomethine dye therefrom has a side absorption at about 430 n.m. and the absorption does not sharply decrease at the longer wavelength region.

Thus, for overcoming these problems, there are provided, for magenta dye image-forming couplers, a pyrazolobenzimidazole skeleton as described in British Pat. No. 1,047,612 and a pyrazolotriazole skeleton as described in U.S. Pat. No. 3,725,067. Also, recently, there is newly provided a 1H-imidazolo[1,2-b]pyrazole skeleton as described in Japanese Patent Application (OPI) No. 162548/84 (U.S. Pat. No. 4,500,630 and European Pat. No. 119741) (the term "OPI" as used herein refers to a "published unexamined Japanese patent application"), a 1H-pyrazolo[1,5-b][1,2,4]-triazole skeleton as described in Japanese Patent Application (OPI) No. 171956/84 (European Pat. No. 0119860), a 1H-pyrazolo[1,5-d]-tetrazole skeleton as described in Japanese Patent Application (OPI) No. 33552/85 (*Research Disclosure*, No. 24220), and a 1H-pyrazolo[1,5]-pyrazole skeleton as described in Japanese Patent Application (OPI) No. 43659/85.

However, although these couplers may overcome the above-described hue problems, there is a problem that since the conversion of the coupler into an azomethine dye is low in the case of processing under the condition of forming a sufficient amount of the oxidation product of an aromatic primary amine developing agent in the silver halide emulsion layer (hereinafter, the conversion is referred to as coloring efficiency), the maximum coloring density (Dmax) is reduced.

For increasing the coloring efficiency, a method of introducing a releasable group at the coupling active position of a coupler, a method of adding a coloring increasing agent, a method of changing the ballast group of the coupler into one fitting to the coupler skeleton, etc., are known.

SUMMARY OF THE INVENTION

An object of this invention is, therefore, to provide a silver halide color photoggraphic material having an improved coloring property (coloring efficiency) using a pyrazoloazole series magenta coupler showing an improved coloring property.

Another object of this invention is to provide a silver halide color photographic material having high sensitivity using a pyrazoloazole series magenta coupler having improved sensitivity.

At the result of various investigations on various linkage groups of magenta couplers, it has been discovered the above-described objects can be attained by a silver halide color photographic material containing a pyrazoloazole series magenta coupler having at least one group expressed by the formula [S] below at a position other than the coupling active position.

$$-(A)_n-L-B \qquad [S]$$

wherein A, L, B and n are defined hereinafter.

DESCRIPTION OF THE PREFERRED EMBODIMENT

Couplers having, for example, $-NHSO_2-$ as a linkage group are known as described in U.S. Pat. Nos. 2,698,795, 2,710,803, etc., and recently acylacetanilide type yellow couplers having $-NHSO_2-$ as the linkage group are described in U.S. Pat. Nos. 3,894,876, 4,256,258, European Patent (EO) No. 17,833A1, etc., phenol- and naphthol-series cyan couplers are described in U.S. Pat. Nos. 4,124,396, 4,334,011, etc., and further 5-pyrazolone series magenta couplers are described in Japanese Patent Publication No. 7039/57, Japanese Patent Application (OPI) Nos. 44,927/76, 146,251/82, etc.

However, there are only a few examples of positively using $-NHSO_2-$ in pyrazoloazole series magenta couplers accoring to this invention, i.e., only U.S. Pat. No. 4,524,450 is known. This U.S. Pat. is characterized in that two sulfonyl groups as a diffusion-resistant group are present and bonded directly to a phenylene group, but these groups are quite distinct from a linkage group of this invention.

It is well known that the effects of the combination of a skeleton of a coupler and a linkage group thereof cannot generally be estimated and the effects can only be determined by practically synthesizing the coupler and using the coupler in a silver halide color photographic material. In particular, the aforesaid fact is more remarkable when the skeleton forming an azomethine dye differs from conventionally known ones and hence it was quite surprising that when a group represented by $-(A)_n-L-B$ as described hereunder was used in a pyrazoloazole series magenta coupler according to this invention, the coloring property was improved.

The above-described pyrazoloazole series magenta coupler according to this invention can be expressed by following general formula [I]

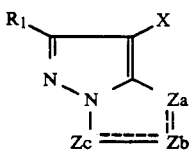

wherein $R_1$ is the same as $R_2$ defined below; X represents a hydrogen atom or a group capable of being released by the coupling reaction with the oxidation product of an aromatic primary amine developing agent; Za, Zb, and Zc each represents a methine group, a substituted methine group, =N—, or —NH—; one of Za—Zb bond and Zb—Zc bond being a double bond and the other being a single bond. When Zb—Zc is a carbon-carbon double bond, the magenta coupler includes the case where Zb—Zc is a part of an aromatic ring. Furthermore, the magenta coupler shown by general formula [I] includes the case in which it forms a dimer, an oligomer or a polymer by $R_1$ or X. Also, when Za, Zb, or Zc is a substituted methine group, the magenta coupler includes the case in which it forms a dimer, an oligomer or a polymer by the substituted methine group.

Further, at least one of $R_1$ and the substituent when Za, Zb, or Zc represents a substituted methine group is a group expressed by the following general formula [S]

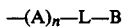

wherein A represents a substituted or unsubstituted alkylene group, a substituted or unsubstituted cycloalkylene group, a substituted or unsubstituted arylene group, or a substituted or unsubstituted aralkylene group, in which in the main chain of said alkylene group, cycloalkylene group, arylene group, or aralkylene group, —O—, —S—, —CO—, —CO$_2$—, —OCO—,

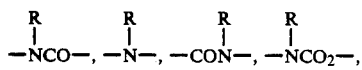

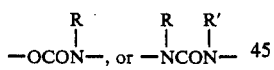

may be contained; L represents

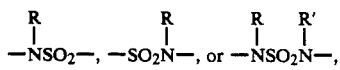

B represents a hydrogen atom or a substituted or unsubstituted alkyl or aryl group which does not contain therein —SO$_2$—; n is 0 or 1; and R and R' each represents a hydrogen atom, a substituted or unsubstituted alkyl group, or a substituted or unsubstituted aryl group.

In the above, in the case that the pyrazoloazole series magenta coupler is a 1H-pyrazole[5,1-c][1,2,4]triazole derivative, A does not represent an aralkylene group containing an arylene group directly connected to L.

When the above-described alkylene group, cycloalkylene group, arylene group, aralkylene group, alkyl group, or aryl group has a substituent, examples of the substituent include a chlorine atom, an alkyl group, an aryl group, a heterocyclic group, a cyano group, an alkoxy group, an aryloxy group, heterocyclic oxy group, an acyloxy group, a carbamoyloxy group, a silyloxy group, a sulfonyloxy group, an acylamino group, an anilino group, a ureido group, an imido group, a sulfamoyl group, a carbamoylamino group, an alkylthio group, an arylthio group, a heterocyclic thio group, an alkoxycarbonylamino group, an aryloxycarbonylamino group, a carbamoyl group, an acyl group, a sulfonyl group, a sulfinyl group, an alkoxycarbonyl group, and an aryloxycarbonyl group.

The oligomer or polymer in general formula [I] means an oligomer or a polymer having two or more moieties shown by general formula [I] in one molecule and includes a bis-compound and a polymer coupler. In this case, the polymer coupler may be a homopolymer composed of monomers (preferably having a vinyl group, hereinafter referred to as a vinyl monomer) only having the moiety shown by general formula [I] or may form a copoylymer with a non-coloring ethylenically unsaturated monomer which does not cause coupling with the oxidation product of an aromatic primary amine developing agent.

The compound shown by general formula [I] is a 5-membered ring-5-membered ring condensed nitrogen heterocyclic ring type coupler and the coloring mother nuclei thereof show an isoelectronic aromatic character with naphthalene and has the chemical structure usually called "azapentalene".

The couplers shown by general formula [I] preferably include 1H-imidazolo[1,2-b]pyrazoles, 1H-pyrazolo[1,5-b]pyrazoles, 1H-pyrazolo[1,5-b]pyrazoles, 1H-pyrazolo[5,1-c][1,2,4]triazoles, 1H-pyrazolo[1,5-b][1,2,4]triazoles, 1H-pyrazolo[1,5-a]tetrazoles, and 1H-pyrazolo[1,5-a]benzimidazoles, and they are represented by the following general formulae (I-1) to (I-6). In these compounds, particularly preferred compounds are those shown by general formula (I-1) and (I-4).

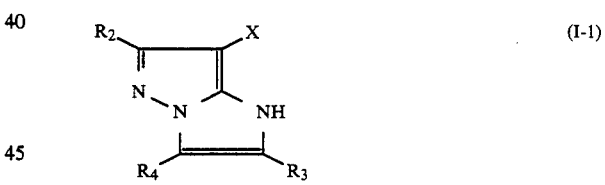

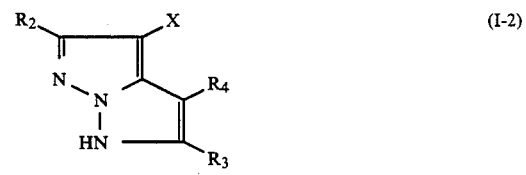

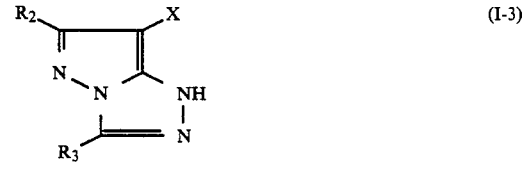

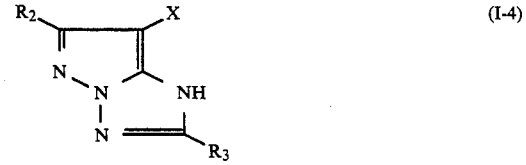

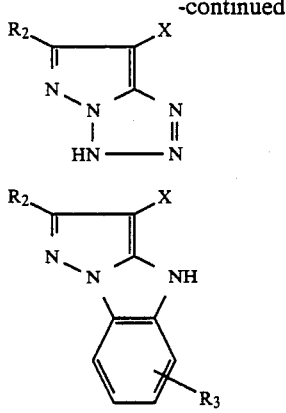

The substituents $R_2$, $R_3$ and $R_4$ in general formulae (I-1) to (I-6) include a hydrogen atom, a halogen atom, an alkyl group, an aryl group, a heterocyclic group, a cyano group, an alkoxy group, an aryloxy group, a heterocyclic oxy group, an acyloxy group, a carbamoyloxy group, a silyloxy group, a sulfonyloxy group, an acylamino group, an anilino group, a ureido group, an imido group, a sulfamoylamino group, a carbamoylamino group, an alkylthio group, an arylthio group, a heterocyclic thio group, an alkoxycarbonylamino group, an aryloxycarbonylamino group, a sulfonamido group, a carbamoyl group, an acyl group, a sulfamoyl group, a sulfonyl group, a sulfinyl group, an alkoxycarbonyl group, or an aryloxycarbonyl group, in which at least one of $R_2$, $R_3$ and $R_4$ represents a group expressed by the foregoing general formula [S]; and X represents a hydrogen atom or a group bonded to a carbon atom at the coupling position through an oxygen atom, a nitrogen atom or a sulfur atom.

The compounds shown by aforesaid general formulae include the case in which $R_2$, $R_3$, $R_4$ or X is a divalent group forming a bis-compound.

Also, when the moiety represented by general formulae (I-1) to (I-6) exists in a vinyl monomer, $R_2$, $R_3$ or $R_4$ represents a simple bond or linkage group and the moiety shown by general formula [I] is bonded to a vinyl group through the bond or linkage group.

More specifically, $R_2$, $R_3$ and $R_4$ in the above formulae include a hydrogen atom, a halogen atom (e.g., a chlorine atom, a bromine atom, etc.,), an alkyl group (e.g., a methyl group, a propyl group, a t-butyl group, a trifluoromethyl group, a tridecyl group, a 3-(2,4-di-t-amylphenoxy)propyl group, a 2-dodecyloxyethyl group, a 3-phenoxypropyl group, a 2-hexylsulfonylethyl group, a cyclopentyl group, a benzyl group, etc.,), an aryl group (e.g., a phenyl group, a 4-t-butylphenyl group, a 2,4-di-t-amylphenyl group, a 4-tetradecanamidophenyl group, ect.,), a heterocyclic (e.g., a 2-furyl group, a 2-thienyl group, a 2-pyrimidinyl group, a 2-benzithiazolyl group, etc.,), a cyano group, an alkoxy group (e.g., a methoxy group, an ethoxy group, a 2-methoxyethoxy group, a 2-dodecyloxyethoxy group, a 2-methanesulfonylethoxy group, etc.,), an aryloxy group (e.g., a phenoxy group, a 2-methylphenoxy group, a 4-t-butylphenoxy group, etc.,), a heterocyclic oxy group (e.g., a 2-benzimidoazolyloxy group, etc.) an acyloxy group (e.g., an acetoxy group, a hexadecanoyloxy group, etc.,), a carbamoyloxy group (e.g., an N-phenylcarbamoyloxy group, an N-ethylcarbamoyloxy group, etc.,), a silyloxy group (e.g., a trimethylsilyloxy group, etc.,), a sulfonyloxy group (e.g., a dodecylsulfonyloxy group, etc.,), an acylamino group (e.g., an acetamido group, a benzamido group, a tetradecanamido group, an α-(2,4-di-5-amylphenoxy)-butylamido group, a α-(3-t-butyl-4-hydroxyphenoxy)-butylamido group, an α-{4-(4-hydroxyphenylsulfonyl)-phenoxy}-decanamido group, etc.), an anilino group (e.g., a phenylamino group, a 2-chloroanilino group, a 2-chloro-5-tetradecanamidoanilino group, a 2-chloro-5-dodecyloxycarbonylanilino group, an N-acetylanilino group, a 2-chloro-5-{α-(3-t-butyl-4-hydroxyphenoxy)-dodecanamido}-anilino group, etc.,), a ureido group (e.g., a phenylureido group, a methylureido group, an N,N-dibutylureido group, etc.,), an imido group (e.g., an N-succinimido group, a 3-benzylhydantoinyl group, a 4-(2-ethylhexanoylamino)phthalimido group, etc.,), a sulfamoylamino group (e.g, an N,N-dipropylsulfamoylamino group, an N-methyl-N-decylsulfamoylamino group, etc.,), a carbamoylamino group (e.g., an N-butylcarbamoylamino group, an N,N-dimethylcarbamoylamino group, etc.), an alkylthio group (e.g., a methylthio group, an octylthio group, a tetradecylthio group, a 2-phenoxyethylthio group, a 3-phenoxypropylthio group, a 3-(4-t-butylphenoxy)propylthio group, etc.,), an arylthio group (e.g., a phenylthio group, a 2-butoxy-5-t-octylphenylthio group, a 3-pentadecylphenylthio group, a 2-carboxyphenylthio group, a 4-tetradecanamidophenylthio group, etc.,), a heterocyclic thio group (e.g., a 2-benzothiazolyl group, etc.,), an alkoxycarbonylamino group (e.g., a methoxycarbonylamino group, a tetradecyloxycarbonylamino group, etc.,), an aryloxycarbonylamino group (e.g., a phenoxycarbonylamino group, a 2,4-di-tert-butylphenoxycarbonylamino group, etc.,), a sulfonamido group (e.g., a methanesulfonamido group, a hexadecanesulfonamido group, a benzenesulfonamido group, a p-toluenesulfonamido group, an octadecanesulfonamido group, a 2-methyloxy-5-t-butylbenzenesulfonamido group, etc.,), a carbamoyl group (e.g., an N-ethylcarbamoyl group, an N,N-dibutylcarbamoyl group, an N-(2-dodecyloxyethyl)carbamoyl group, an N-methyl-N-dodecylcarbamoyl group, N-{3-(2,4-di-tert-amylphenoxy)propyl}carbamoyl group, etc.,), an acyl group (e.g., an acetyl group, a (2,4-di-tert-amylphenoxy)acetyl group, a benzoyl group, etc.,), a sulfamoyl group (e.g., an N-ethylsulfamoyl group, an N,N-dipropylsulfamoyl group, an N-(2-dodecyloxyethyl)sulfamoyl group, an N-ethyl-N-dodecylsulfamoyl group, an N,N-diethylsulfamoyl group, etc.,), a sulfonyl group (e.g., a methanesulfonyl group, an octanesulfonyl group, a benzenesulfonyl group, a tolenesulfonyl group, etc.,), a sulfinyl group (e.g., an octanesulfinyl group, a dodecylsulfinyl group, a phenylsulfinyl group, etc.,), an alkoxycarbonyl group (e.g., a methoxycarbonyl group, a butyloxycarbonyl group, a dedecylcarbonyl group, an octadecylcarbonyl group, etc.,), an an aryloxycarbonyl group (e.g., a phenyloxycarbonyl group, a 3-pentadecyloxycarbonyl group, etc.,).

The group expressed by the general formula, —(A)-$n$—L—B is explained below in detail.

A represents a substituted or unsubstituted alkylene group (e.g., a methylene group, an ethylene group, a 1,3-propylene group, a 1,2-propylene group, a 1,4-butylene group, a 2,3-butylene group, a 2,2-dimethylethylene group, a 2-phenylethylene group, a 1,1,2,2-tetrafluoroethylene group, a 2-acetamidoethylene group, a 2-methanesulfonamidoethylene group, a 2-methoxyethylene group, etc.), a substituted or unsubstituted cycloalkylene group (e.g., a 1,4-cyclohexylene group, a 1,3-cyclopentalene group, a 1-methyl-1,4-cyclohexylene group, a 1-phenyl-1,4-cyclohexylene group, a 2,2-dichloro-1,4-cyclohexylene group, etc.), a substituted or unsubstituted arylene group (e.g., a 1,4-phenylene group, a 1,3-phenylene group, a 4-chloro-1,3-phenylene group, a 4-acetamido-1,2-phenylene group, a 2,3,5,6-tetrafluoro-1,4-phenylene group, etc.), or a substituted or unsubstituted aralkylene group

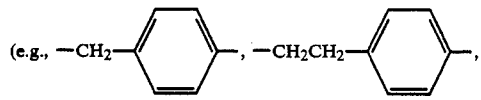

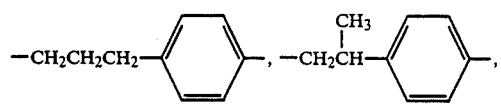

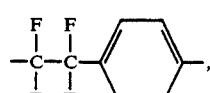

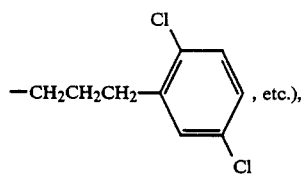

in which in the main chain of said alkylene group, cycloalkylene group, arylene group, or aralkylene group, —O—, —S—, —CO—, —CO$_2$, —OCO—,

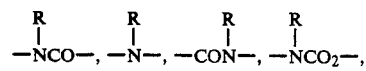

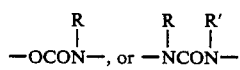

wherein R and R' each represents a hydrogen atom, a substituted or unsubstituted alkyl group (e.g., a methyl group, an ethyl group, an n-octyl group, a hexadecyl group, a 2-methoxyethyl group, a benzyl group, a 2-chloroethyl group, a 3-phenoxypropyl group, etc.), or a substituted or unsubstituted aryl group (e.g., a phenyl group, a 4-methylphenyl group, a 3,5-dichlorophenyl group, a 4-acetamidophenyl group, a 3-methoxyphenyl group, etc.), may be contained (examples of such groups include

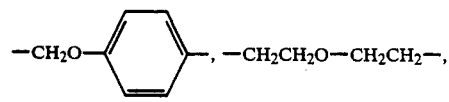

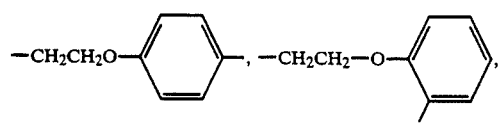

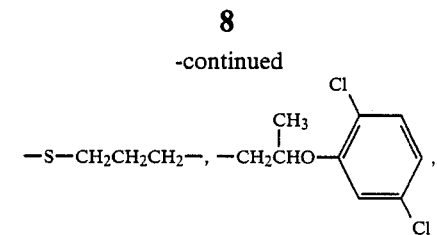

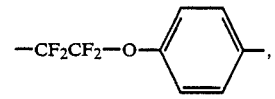

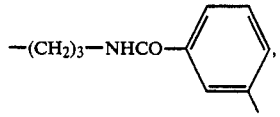

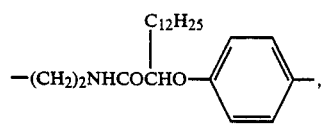

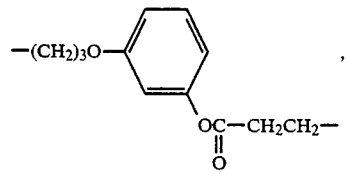

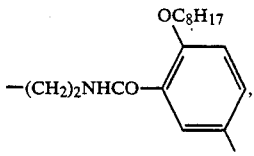

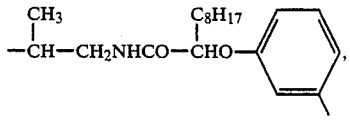

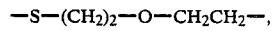

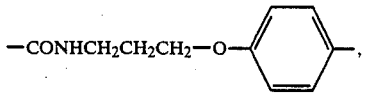

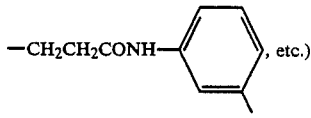

L represents —NSO$_2$—, —SO$_2$N—, or —NSO$_2$N—, in which R and R' are the same as defined above. Among them, those in which either one of R or R' represents a hydrogen atom are preferred.

B represents a hydrogen atom, a substituted or unsubstituted alkyl group which does not contain therein —SO$_2$— (e.g., a methyl group, a dodecyl group, a 2-ethylhexyl group, a 3-(2,4-di-tert-pentylphenoxy)propyl group, a trifluoromethyl group, a benzyl group, etc.), or a substituted or unsubstituted aryl group which does not contain therein —SO$_2$— (e.g., a phenyl group, a 4-dodecyloxyphenyl group, a 2,5-dioctylphenyl group, a 2-chloro-5-dodecanamidophenyl group, a 4-dodecylphenyl group, a 2-methyl-5-dodecyloxyphenyl group, a 2-octyloxy-5-tert-octylphenyl group, a 2,4-dioctylphenyl group, a 2-(2-methoxyethoxy)-5-tert-octylphenyl group, a 2,4-bis(2-butoxyethoxy)phenyl group, a 2,5-bis[2-(2-ethoxyethoxy)ethoxy]phenyl group, a 4-(2-ethylhexyloxy)naphthyl group, etc.).

n is 0 or 1.

As the group expressed by the general formula [S], a group expressed by the following general formula [S-1] is preferred.

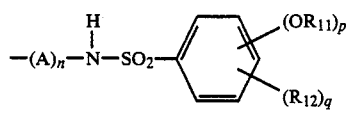
[S-1]

In the general formula [S-1], A and n each has the same meaning as defined above for the general formula [S]; $R_{11}$ represents a hydrogen atom, an alkyl group, a cycloalkyl group, an aryl group, an aralkyl group, or an acyl group; $R_{12}$ has the same meaning as for the substituent of the substituted aryl group for B in the general formula [S]; p represents an integer of from 1 to 5; q represents an integer of from 0 to 4; and p+q is an integer of from 1 to 5.

In the general formula [S-1], the adjacent substituents on the benzene nucleus may jointly form a 5- or 6-membered ring.

As the group expressed by the general formula [S], a group expressed by the following general formula [S-2] or [S-3] is more preferred.

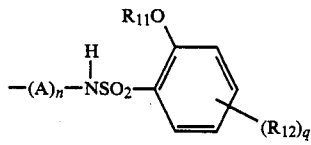
[S-2]

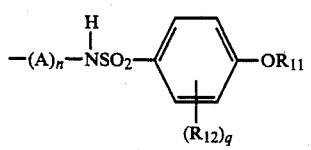
[S-3]

In the above general formulae [S-2] and [S-3], A, $R_{11}$, $R_{12}$, n, and q are the same as defined for the general formula [S-1].

In the case that the pyrazoloazole series magenta coupler of this invention is expressed by the general formula (I-3), the group expressed by the general formula [S] is most preferably one expressed by the general formula [S-2].

Among the groups expressd by the general formulae [S-2] and [S-3], those in which $R_{11}$ represents an alkyl group are particularly preferred.

Further, in the case that the pyrazoloazole series magenta coupler of this invention is expressed by the general formula (I-4) (i.e., a 1H-pyrazolo[5,1-c][1,2,4]triazole), A in the general formula [S] does not represent an aralkylene group containing an arylene group directly connected to L. Specifically, A excludes, for example,

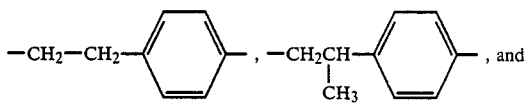

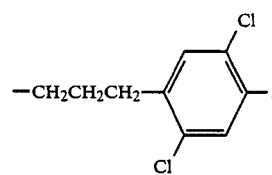

Specific examples of the group expressed by the general formula [S] are shown below but they are not limited to these specific compounds.

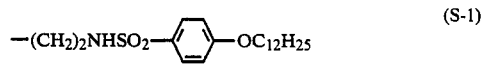
(S-1)

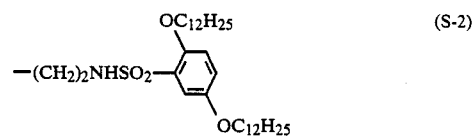
(S-2)

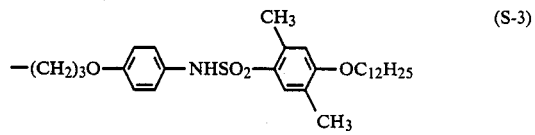
(S-3)

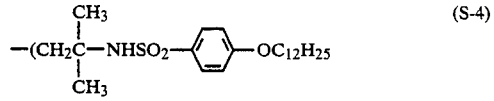
(S-4)

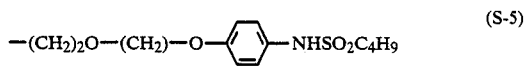
(S-5)

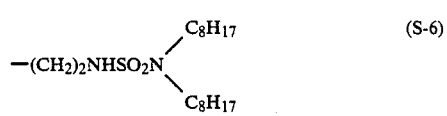
(S-6)

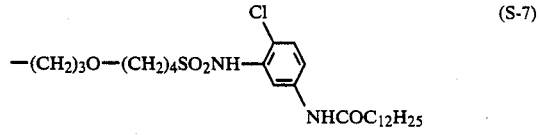
(S-7)

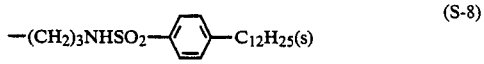
(S-8)

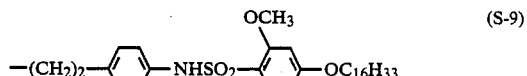
(S-9)

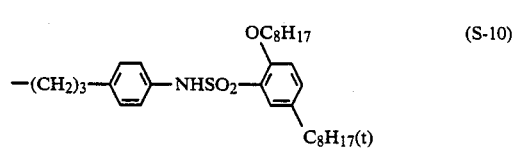
(S-10)

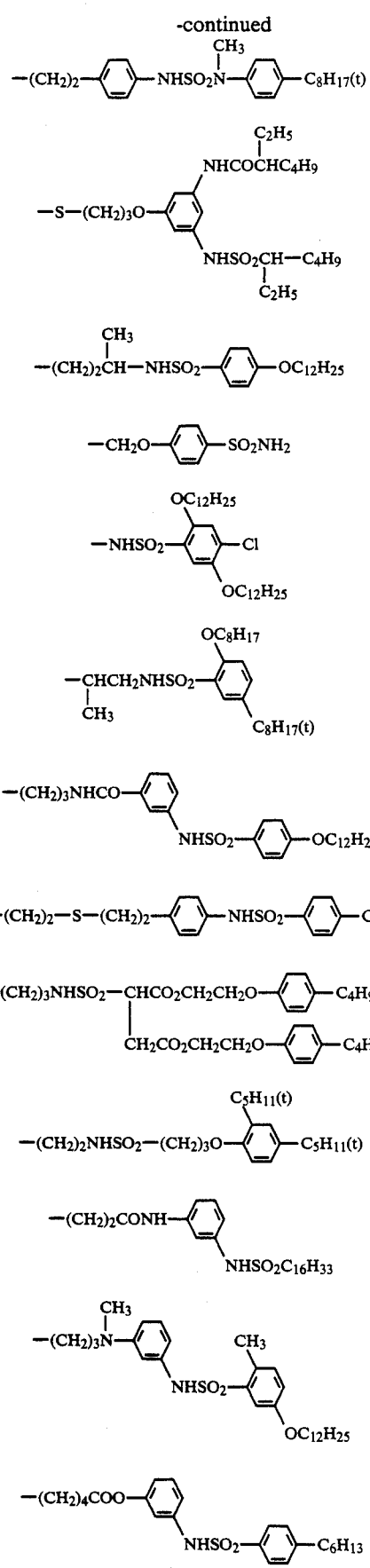

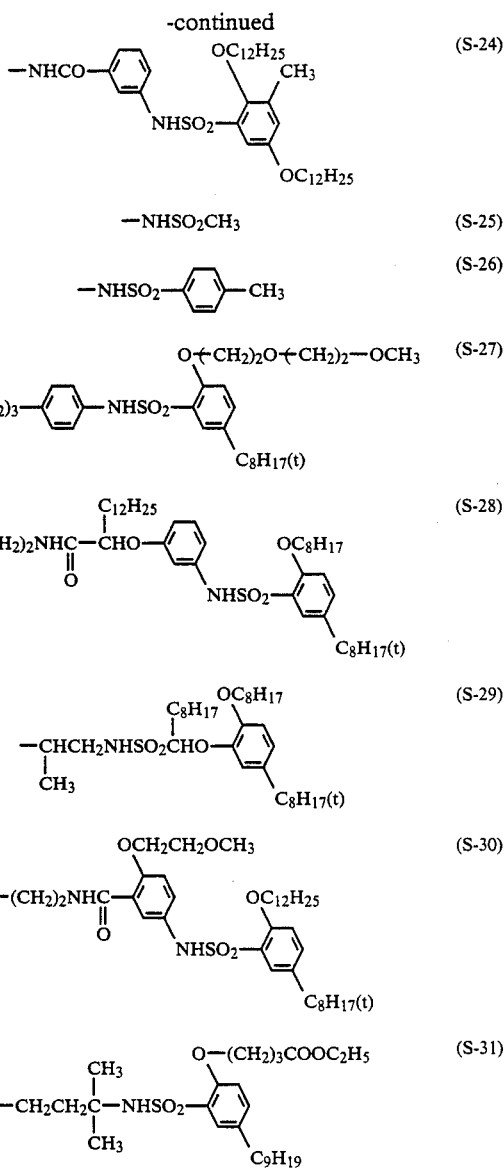

Now, X in the above-described general formulae is explained below in detail. That is, X represents a hydrogen atom, a halogen atom (e.g., a chlorine atom, a bromine atom, an iodine atom, etc.), a carboxy group, a group bonded by an oxygen atom (e.g., an acetoxy group, a propanoyloxy group, a benzoyloxy group, a 2,4-dichlorobenzoyloxy group, an ethoxyoxaloyloxy group, a vinyloxy group, a cinnamoyloxy group, a phenoxy group, a 4-cyanophenoxy group, a 4-methanesulfonamidophenoxy group, a 4-methanesulfonylphenoxy group, an α-naphthoxy group, a 3-pentadecylphenoxy group, a benzyloxycarbonyloxy group, an ethoxy group, a 2-cyanoethoxy group, a benzyloxy group, a 2-phenethyloxy group, a 2-phenoxyethoxy group, a 5-phenyltetrazolyloxy group, a 2-benzothiazolyloxy group, etc.), a group bonded by a nitrogen atom (e.g., a 1-piperidyl group, a 5,5-dimethyl-2,4-dioxo-3-oxazolidinyl group, a 1-benzylethoxy-3-hydantoinyl group, a 2N-1,1-dioxo-3(2H)-oxo-1,2-benzoisothiazolyl group, a 2-oxo-1,2-dihydro-1-pyridinyl group, an imidazolyl group, a pyrazolyl group, a 3,5-diethyl-1,2,4-triazol-1-yl group, a 5- or 6-bromo-benzotriazol-1-yl group, a 5- methyl-1,2,3,4-tetraazol-1-ly group, a benzimdiazolyl group, a 3-benzyl-1-hydantoinyl group, a 1-benzyl-5-hexadecyloxy-3-hydantoinyl group, a 5-methyl-1-tetrazolyl group, a 4-methoxyphenylazo group, a 4-pivaloylaminophenylazo group, a 2-hydroxy-4-propanoylphenylazo group, etc.), or a group bonded by a sulfur atom (e.g., a phenylthio group, a 2-carboxyphenylthio group, a 2-methoxy-5-t-octylphenylthio group, a 4-methanesulfonylphenylthio group, a 4-octanesulfonamidophenylthio group, a 2-butoxyphenylthio group, a 2-(2-hexanesulfonylethyl)-5-tert-octylphenylthio group, a benzylthio group, a 2-cyanoethylthio group, a 1-ethoxycarbonyltridecylthio group, a 5-phenyl-2,3,4,5,-tetrazolylthio group, a 2-benzothiazolylthio group, a 2-dodecylthio-5-thiophenylthio group, a 2-phenyl-3-dodecyl-1,2,4-triazolyl-5-thio group, etc.).

Also, when $R_2$, $R_3$, $R_4$ or X is a divalent group to structure a bis form, the divalent group includes a substituted or unsubstituted alkylene group (e.g., a methylene group, an ethylene group, a 1,10-decylene group, $-CH_2CH_2O-CH_2CH_2-$, etc.), a substituted or unsubstituted phenylene group (e.g., a 1,4-phenylene group, a 1,3-phenylene group,

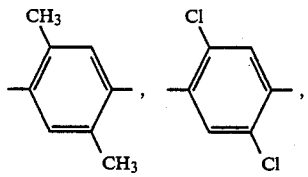

etc.), or $-NHCO-R_5-CONH-$ (wherein $R_5$ represents a substituted or unsubstituted alkylene group or a substituted or unsubstituted phenylene group.

When the compound shown by general formulae (I-1) to (I-6) exists in a vinyl monomer, the linkage group shown by $R_2$, $R_3$, or $R_4$ includes a group formed by combining the groups selected from an alkylene group (substituted or unsubstituted alkylene group, such as a methylene group, an ethylene group, a 1,10-decylene group, $-CH_2CH_2OCH_2CH_2-$,), a phenylene group (substituted or unsubstituted phenylene group such as a 1,4-phenylene group, a 1,3-phenylene group,

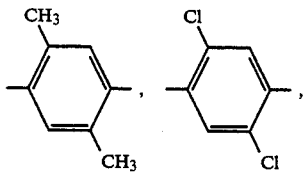

etc.), $-NHCO-$, $-CONH-$, $-O-$, $-OCO-$, and an aralkylene group

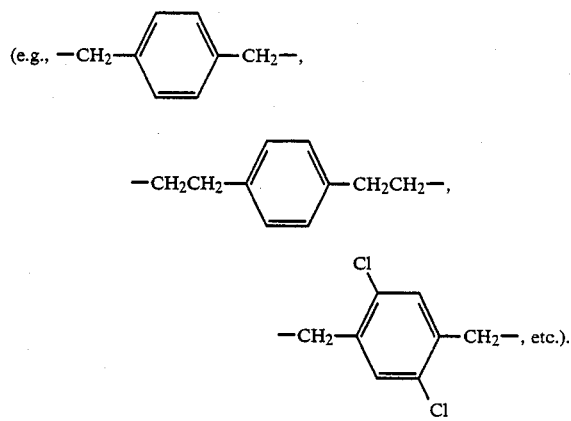

In addition, the vinyl group in the vinyl monomer includes vinyl monomers having substituents in addition to the substituents described above in regard to general formulae (I-1) to (I-6). Preferred substituents for the vinyl groups are a hydrogen atom, a chlorine atom, or an alkyl group having 1 to 9 carbon atoms.

Examples of the non-coloring ethylenically unsaturated monomer which does not cause coupling with the oxidation product of an aromatic primary amine developing agent are α-alacrylic acids such as acrylic acid, α-chloroacrylic acid, methacrylic acid, etc; esters or amides formed from such alacrylic acids; vinyl esters, aromatic vinyl compounds, itaconic acid, maleic acid, maleic anhydride, maleic acid esters, N-vinyl-2-pyrrolidone, N-vinylpyridine, 2- and 4-vinylpyridines, etc.

In this case, two or more kinds of the non-coloring ethylenically unsaturated monomers may be used together.

The specific compounds of the couplers shown by above-described general formulae (I-1) to (I-6) and the synthesis methods therefor are described in the following publications.

That is, the compounds shown by general formula (I-1) are described in Japanese Patent Application (OPI) No. 162548/84 (U.S. Pat. No. 4,500,630 and European Pat. No. 119741), the compounds shown by general formula (I-2) in Japanese Patent Application (OPI) No. 43659/85, the compounds shown by general formula (I-3) in Japanese Patent Publication No. 27411/72, the compounds shown by general formula (I-4) in Japanese Patent Application (OPI) No. 171956/84 (European Pat. No. 0119860) and Japanese Patent Application No. 27,745/84 (U.S. Application Ser. No. 702,691, filed Feb. 19, 1985), and the compounds shown by general formula (I-6) in U.S. Pat. No. 3,061,432.

Now, specific examples of the pyrazoloazole couplers for use in this invention are shown below but they are not limited to these specific compounds.

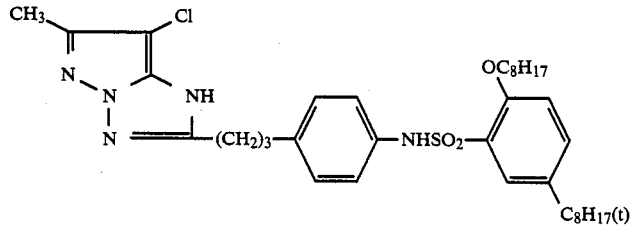

(1)

-continued
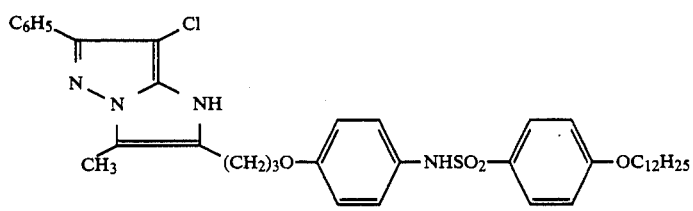
(2)
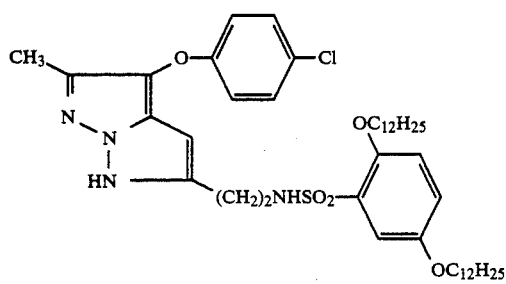
(3)
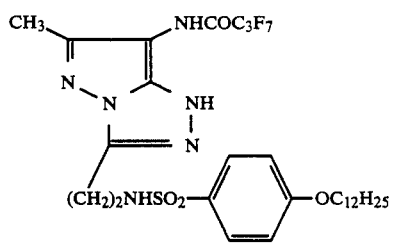
(4)
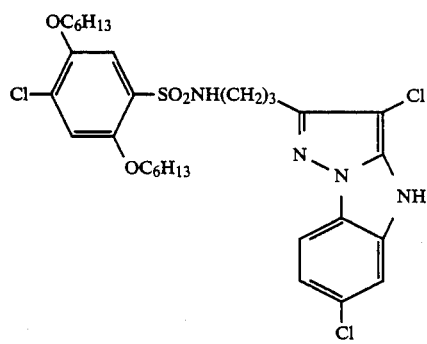
(5)
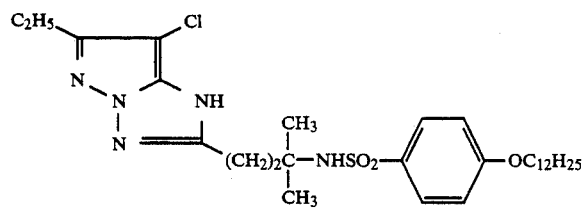
(6)
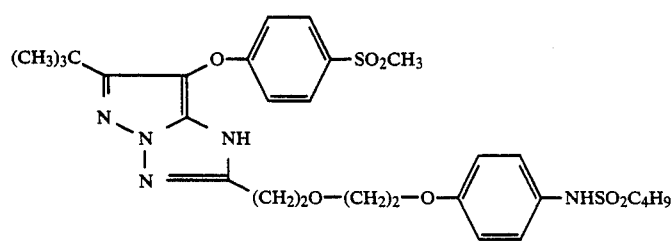
(7)

-continued
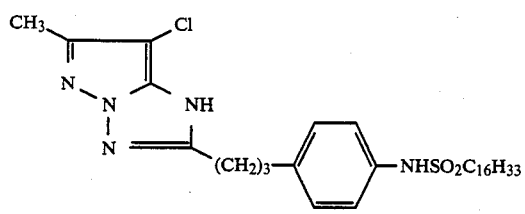
(8)
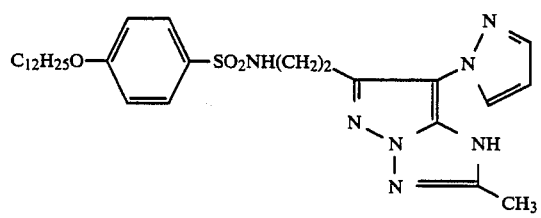
(9)
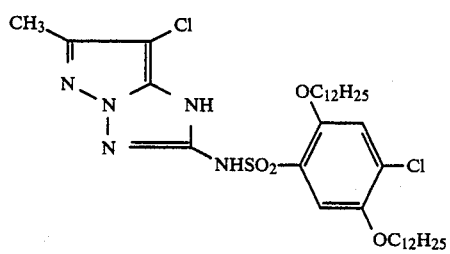
(10)
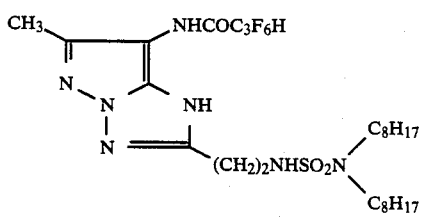
(11)
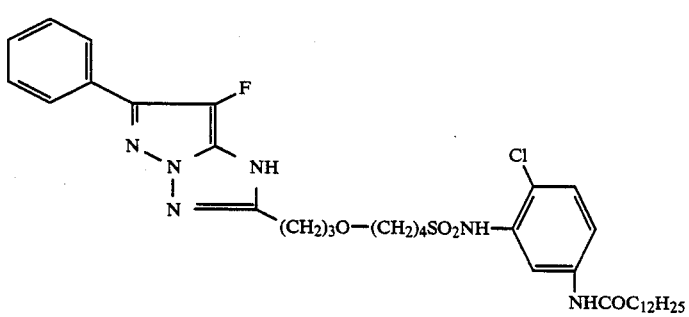
(12)
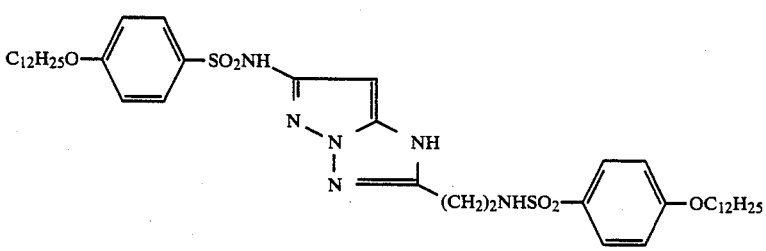
(13)

-continued
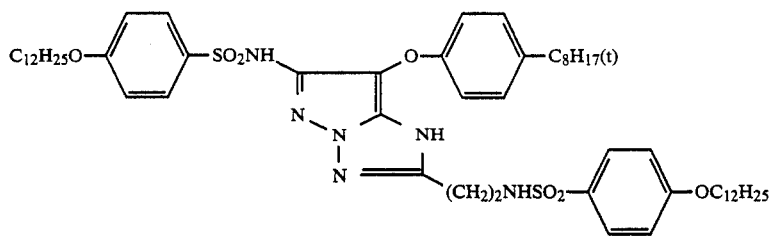
(14)
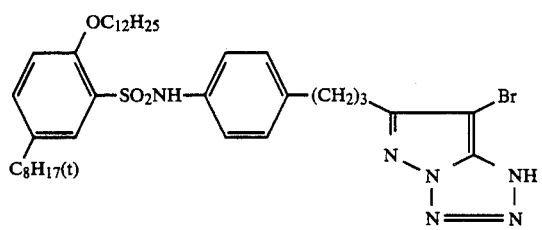
(15)
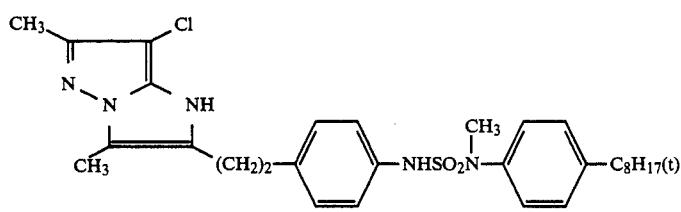
(16)
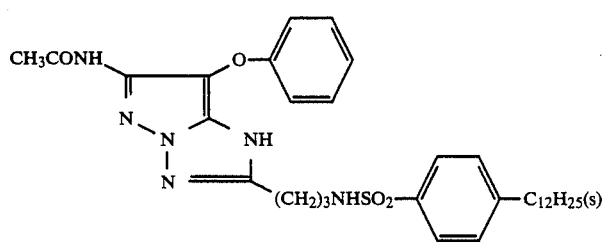
(17)
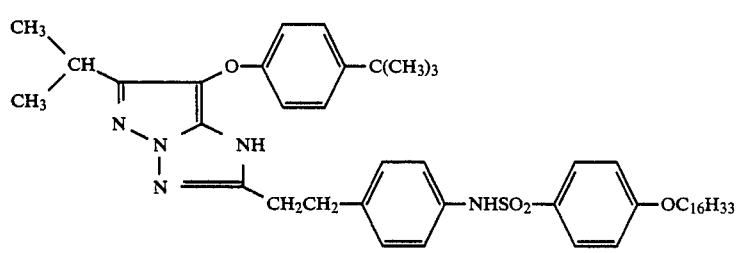
(18)
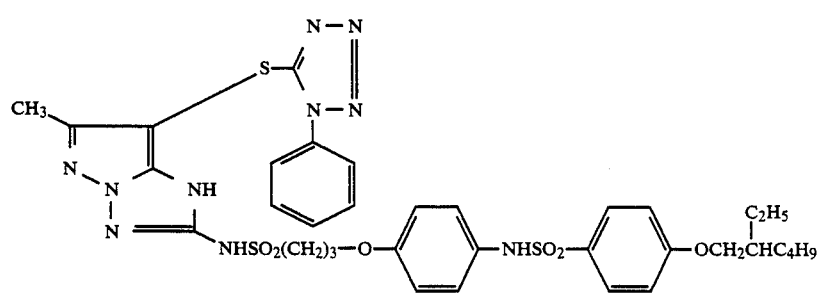
(19)

-continued
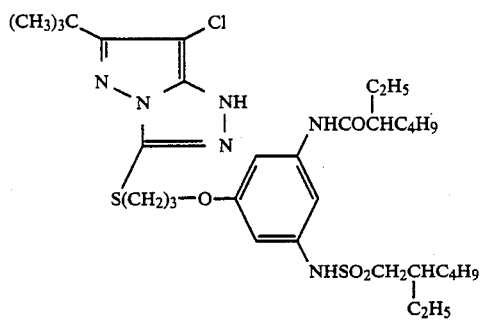 (20)
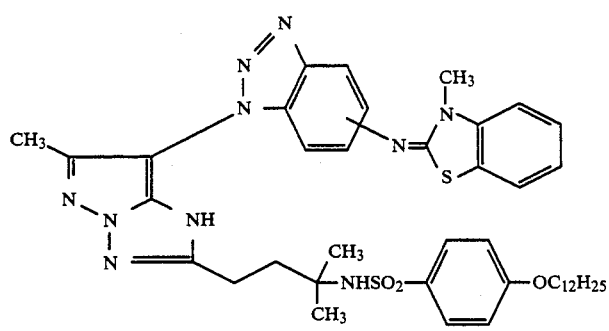 (21)
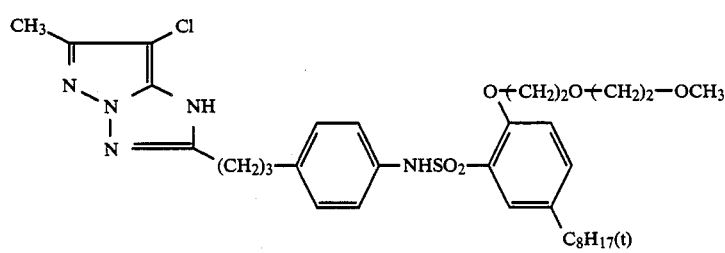 (22)
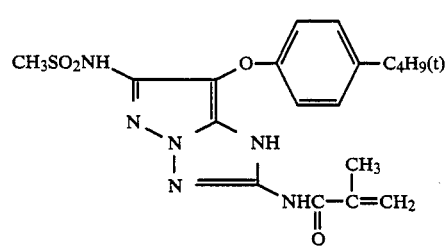 (23)
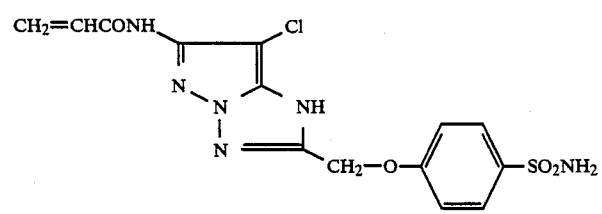 (24)
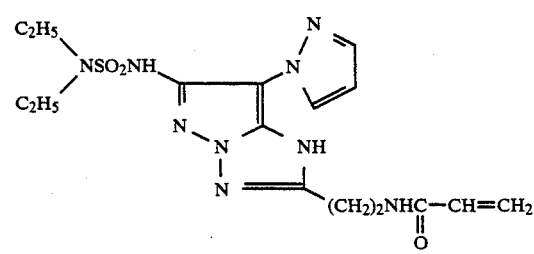 (25)

-continued
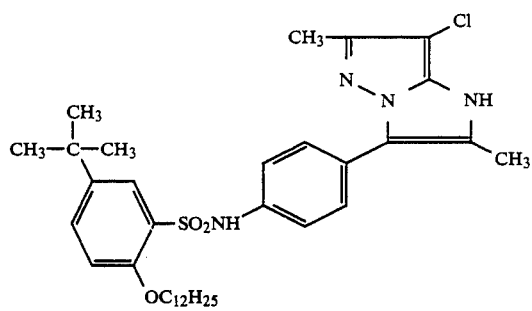
(26)
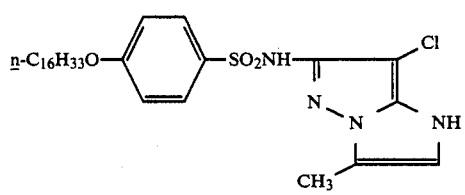
(27)
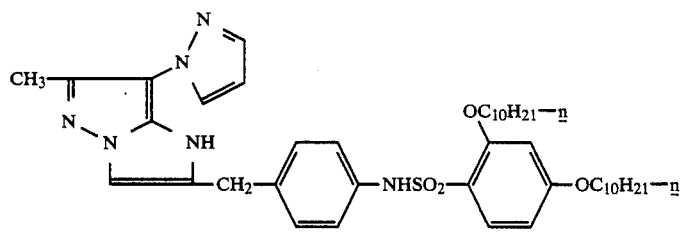
(28)
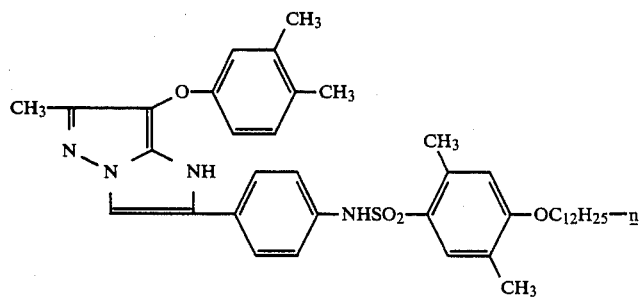
(29)
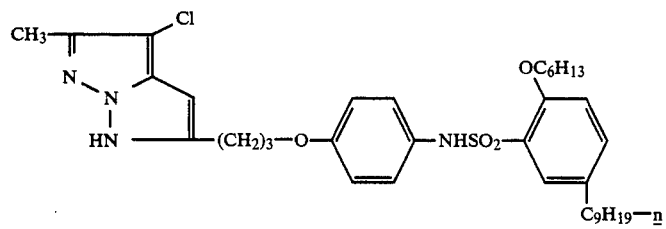
(30)
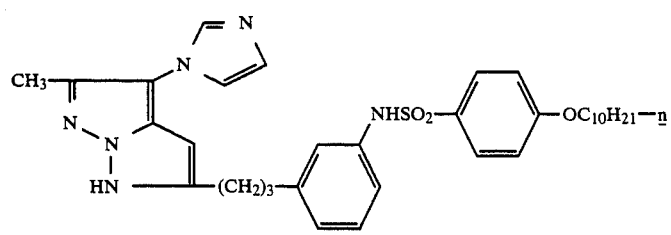
(31)

-continued
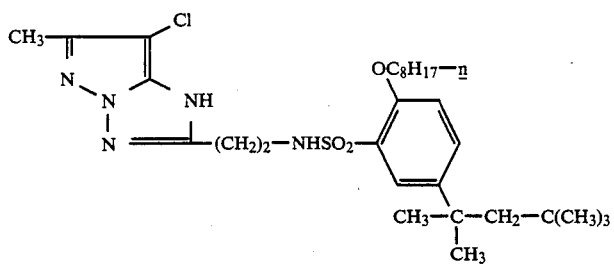
(32)
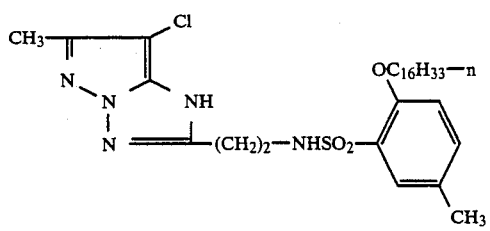
(33)
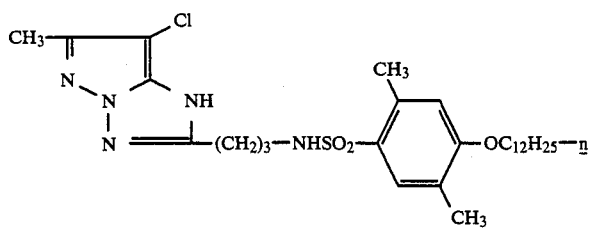
(34)
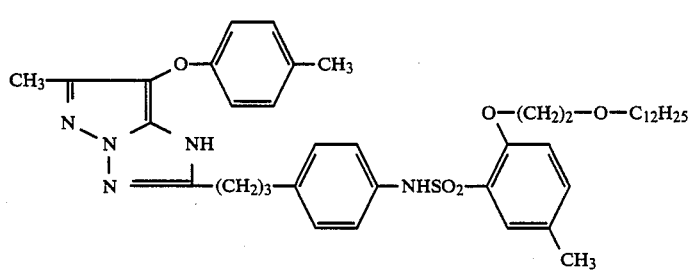
(35)
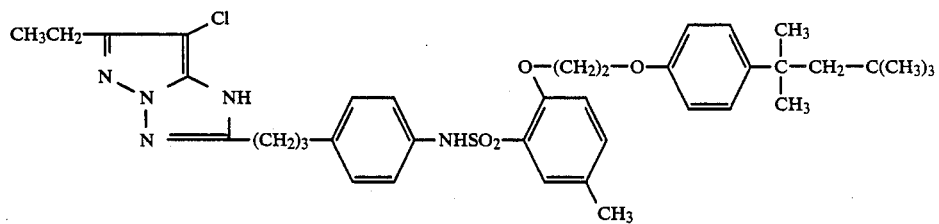
(36)
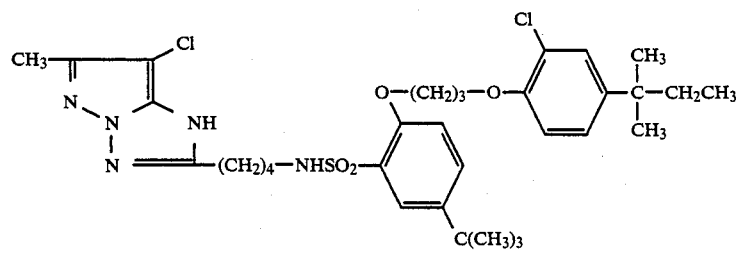
(37)

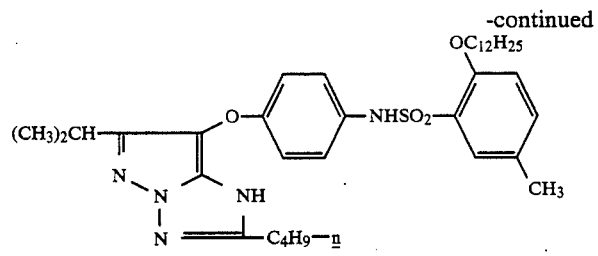 (38)
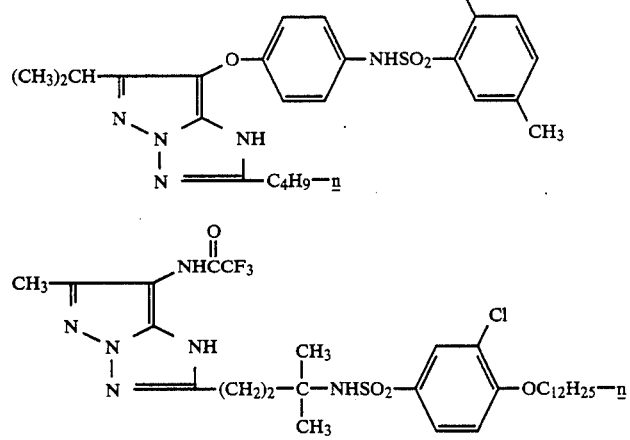 (39)
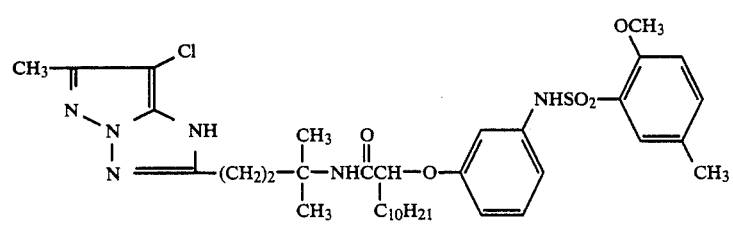 (40)
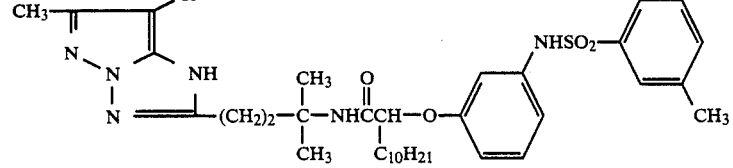 (41)
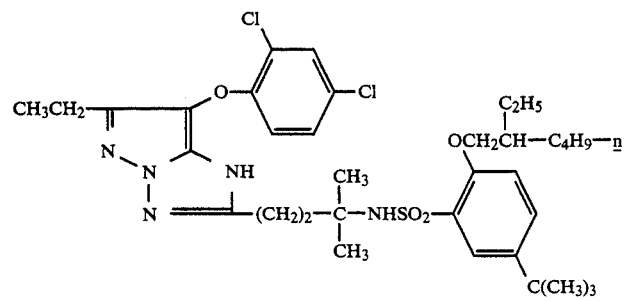 (42)
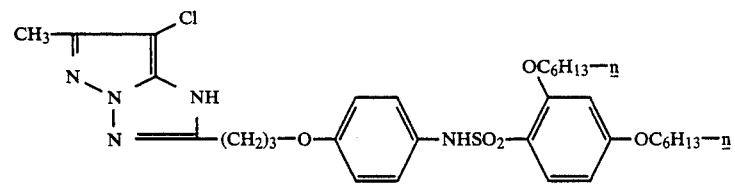 (43)
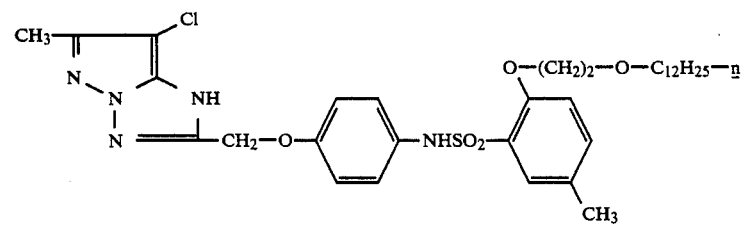 (44)
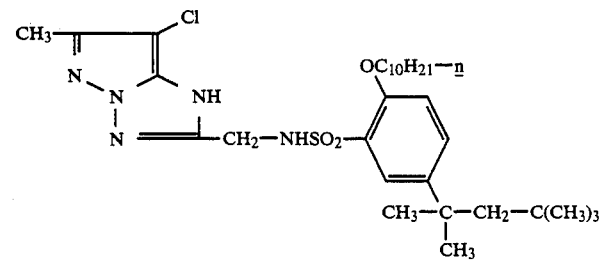

-continued
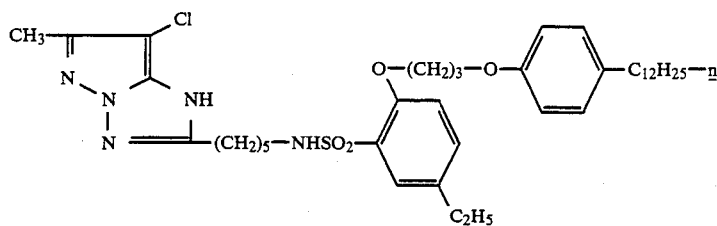 (45)
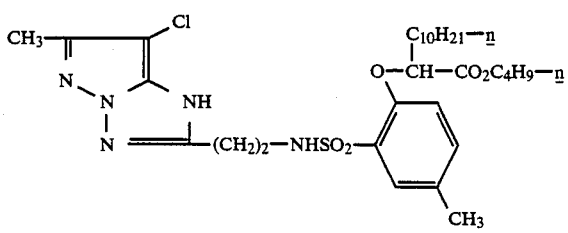 (46)
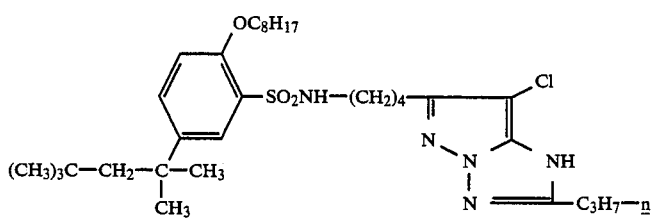 (47)
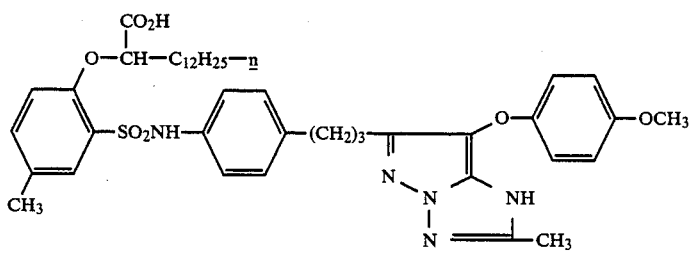 (48)
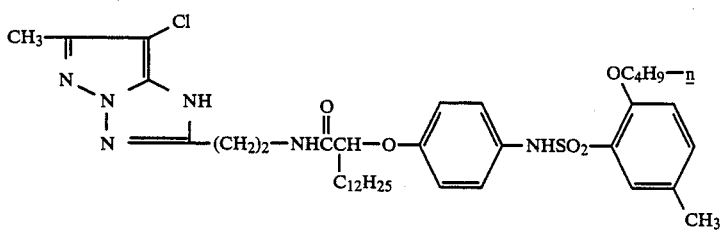 (49)
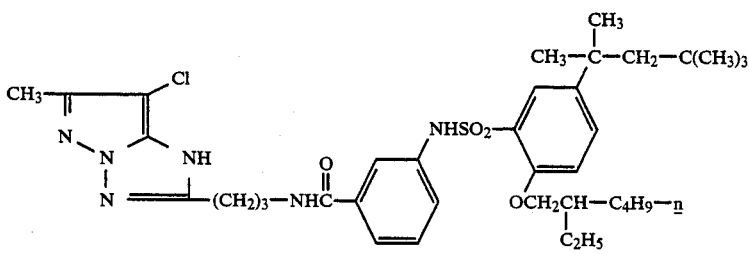 (50)

-continued
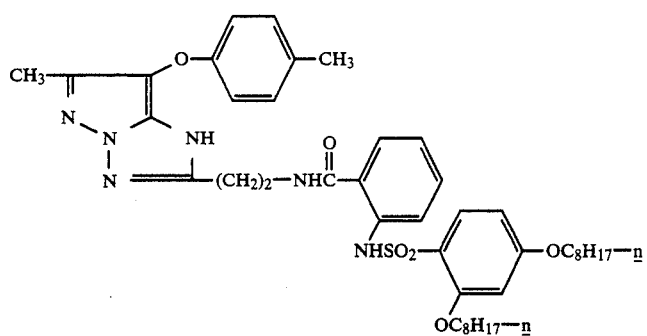 (51)
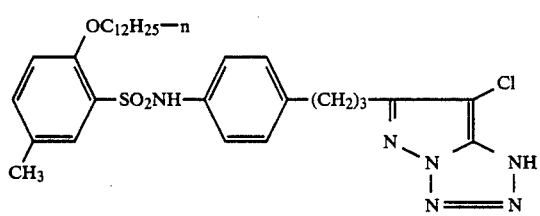 (52)
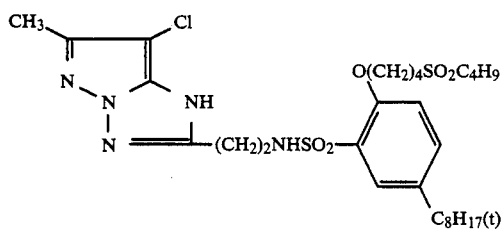 (53)
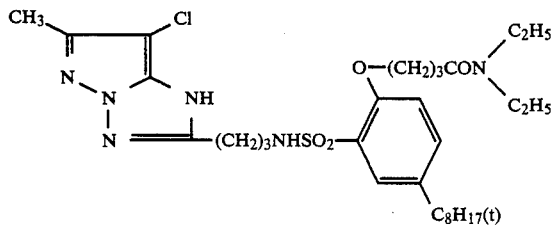 (54)
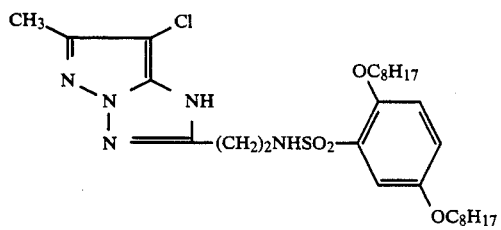 (55)
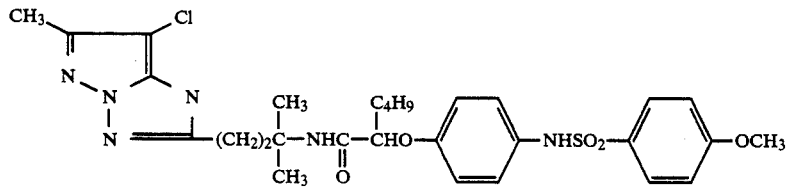 (56)
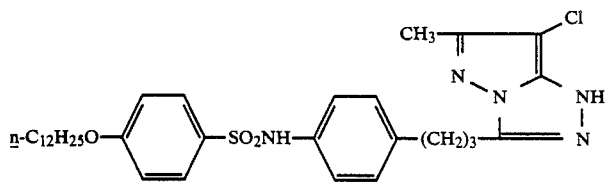 (57)

-continued
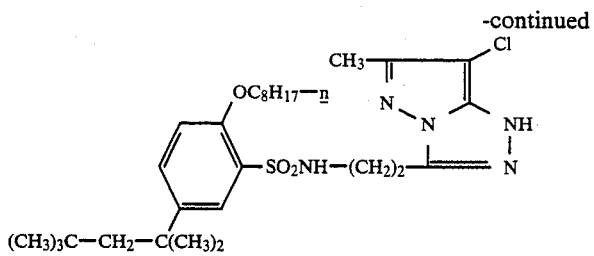 (58)
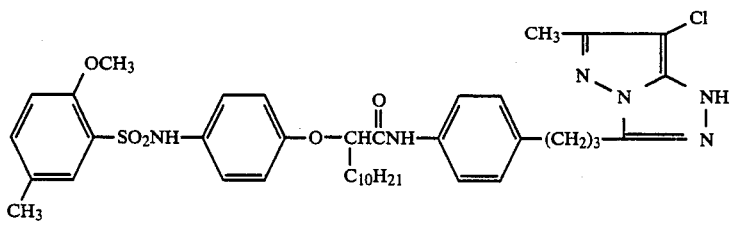 (59)
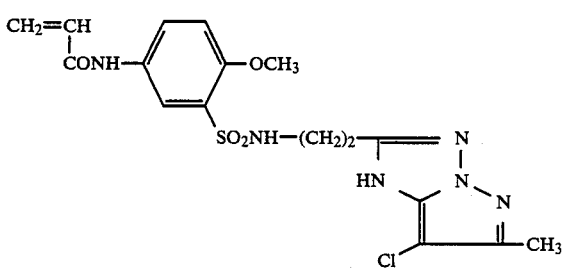 (60)
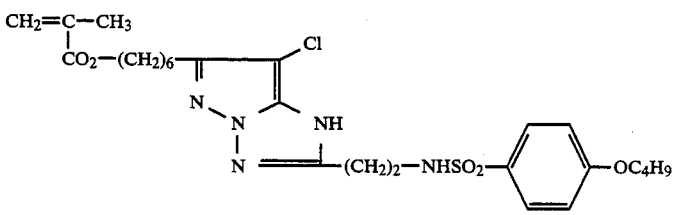 (61)
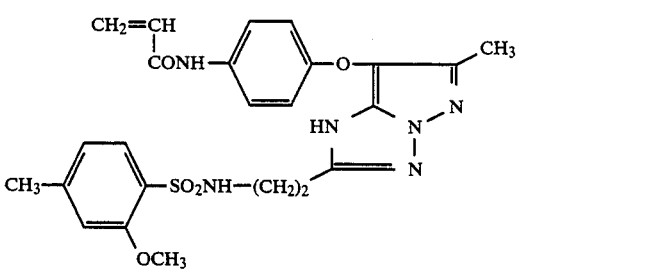 (62)
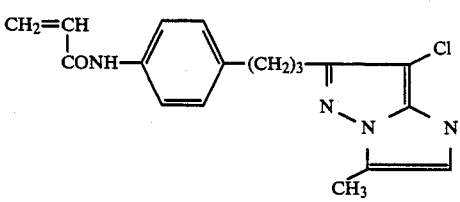 (63)
Now, specific examples of synthesis examples of the couplers for use in this invention as illustrated above are explained.
Synthesis Example 1 [Synthesis of Coupler (1)]

zenesulfonyl chloride (Compound B). The crude product was used as it was in the subsequent reaction.

(2) Synthesis of Coupler (1)

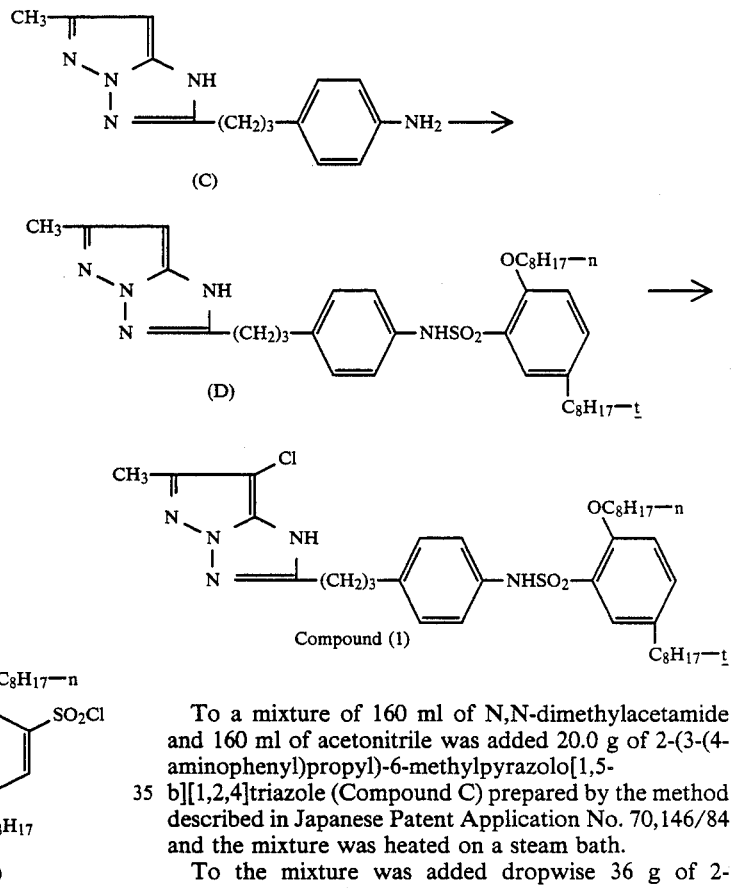

To a mixture of 160 ml of N,N-dimethylacetamide and 160 ml of acetonitrile was added 20.0 g of 2-(3-(4-aminophenyl)propyl)-6-methylpyrazolo[1,5-b][1,2,4]triazole (Compound C) prepared by the method described in Japanese Patent Application No. 70,146/84 and the mixture was heated on a steam bath.

To the mixture was added dropwise 36 g of 2-octyloxy-5-t-octylbenzenesulfonyl chloride (compound B) and the mixture was stirred for 30 minutes. After cooling the reaction mixture, 1.0 liter of water was added thereto and the product obtained was extracted with ethyl acetate. The organic layer thus obtained was dried on anhydrous magnesium sulfate, concentrated, and subjected to silica gel column chromatography (eluent: chloroform/ethyl acetate=5/1). The eluate obtained was concentrated to provide 22.8 g (46%) of Compound D.

In 300 ml of dichloromethane was dissolved 22.1 g of Compound D obtained above, the solution was stirred at room temperature, and after adding thereto 4.51 g of N-chlorosuccinic acid imide, the mixture was stirred for 30 minutes. The reaction mixture thus obtained was washed three times with 500 ml of water, dried on anhydrous magnesium sulfate, concentrated and then recrystallized from acetonitrile to provide 18.9 g (81%) of Compound (1) as light brown crystals (m.p. 114°–115° C.).

Elemental Analysis:

|  | C | H | N |
|---|---|---|---|
| Calculated: | 64.50% | 7.82% | 10.45% |
| Found: | 64.26% | 7.91% | 10.49% |

Magnetic Resonance Spectra (CDCL$_3$):

(ppm): 11.60 (1H, br), 7.72 (1H, d, J=3 Hz), 7.42 (1H, dd, J=3.9 Hz), 7.0–6.8 (6H, m), 4.15 (2h, t, J=6.6 Hz), To 700 ml of N,N-dimethylformamide were added 206 g of 4-t-octylphenol and 207 g of anhydrous potassium carbonate and the mixture was stirred at 50° C. To the mixture was added dropwise 251 g of 1-bromooctane and thereafter the mixture was stirred for 7 hours at 65° to 80° C. Then, after removing insoluble matter by filtration, water was added to the filtrate thus obtained and the product was extracted with ethyl acetate. The organic solvent layer was collected, washed with a saturated aqueous sodium chloride solution, dried on anhydrous magnesium sulfate, and concentrated under reduced pressure. The oily material thus obtained was distilled under reduced pressure (169°–172° C./0.05–0.06 mmHg) to provide 257 g (81% in yield) of 1-octyloxy-4-t-octylbenzene (Compound A).

In 900 ml of dichloromethane was dissolved 159 g of Compound A and the solution was stirred while cooling with an ice bath. After slowly adding dropwise 41.5 ml of chlorosulfonic acid to the solution, the mixture was stirred for 1.5 hours. Then, dichloromethane was removed while reducing the pressure by a tap aspirator and 480 ml of N,N-dimethylacetamide and 150 ml of acetonitrile were added to the residue formed. After adding dropwise 93.2 ml of phosphorous oxychloride to the mixture over a period of 40 minutes, the resultant mixture was stirred for 1.5 hours at 40° C. The solution was extracted four times with 500 ml of hexane and the hexane layer was collected and concentrated to provide 229 g of a crude product of 2-octyloxy-5-t-octylben- 2.9–2.4 (4H, m). 2.33 (3H, S), 2.2–1.8 (4H, m), 1.7–1.1 (21H, m), 0.87 (3H, br), 0.48 (9H, S).

Synthesis Example 2 [synthesis of Coupler (22)]

(1) Synthesis of 2-(2-(2-methoxyethoxy)ethoxy)-5-t-octylbenzenesulfonyl chloride (Compound F):

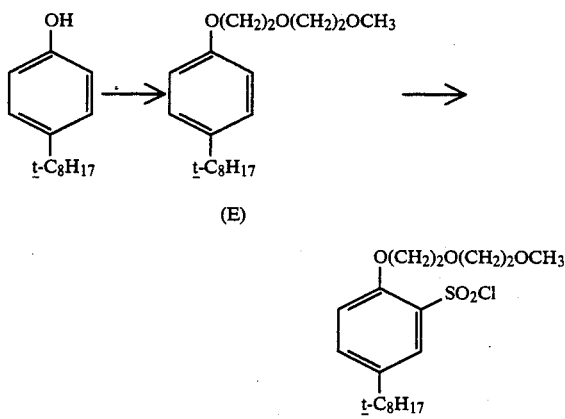

To 2.0 liters of N,N-dimethylformamide were added 685 g of 4-t-octylphenol and 797 g of anhydrous potassium carbonate and the mixture was heated to 100° C. with stirring. To the mixture was added dropwise 549 g of 1-(2-methoxyethoxy)-2-chloroethane over a period of 1.5 hours and the mixture was further stirred for 5 hours at 125° to 130° C. After cooling, insoluble matter was filtered away, water was added to the filtrate thus obtained, and the product was extracted with ethyl acetate. The organic solvent layer was collected, dried on anhydrous sodium sulfate, and then concentrated under reduced pressure. The oily product thus obtained was distilled under reduced pressure (152°–160° C./0.015 mmHg) to provide 918 g (90%) of Compound E.

In 300 ml of dichloromethane was dissolved 55 g of Compound E obtained above and the solution was cooled by an ice bath with stirring. To the solution was slowly added dropwise 23 ml of chlorosulfonic acid and the mixture was stirred for 1.5 hours at the same temperature. Then, the ice bath was removed from the system and after adding 160 ml of N,N-dimethylacetamide and 50 ml of acetonitrile to the mixture, the resultant mixture was stirred at 30° C. To the mixture was added dropwise 32 ml of phosphorus oxychloride and the resultant mixture was stirred for 2 hours at 35° to 45° C. The reaction mixture thus obtained was poured into ice water and extracted with ethyl acetate. The organic solvent layer thus formed was collected, washed twice with a saturated sodium chloride solution, dried by anhydrous sodium sulfate, and then concentrated under reduced pressure to provide 77 g of the crude product of 2-(2-(2-methoxyethoxy)ethoxy)-5-t-octylbenzenesulfonyl chloride (Compound F). The crude product was used as it was for the subsequent reaction.

(2) Synthesis of Coupler (22)

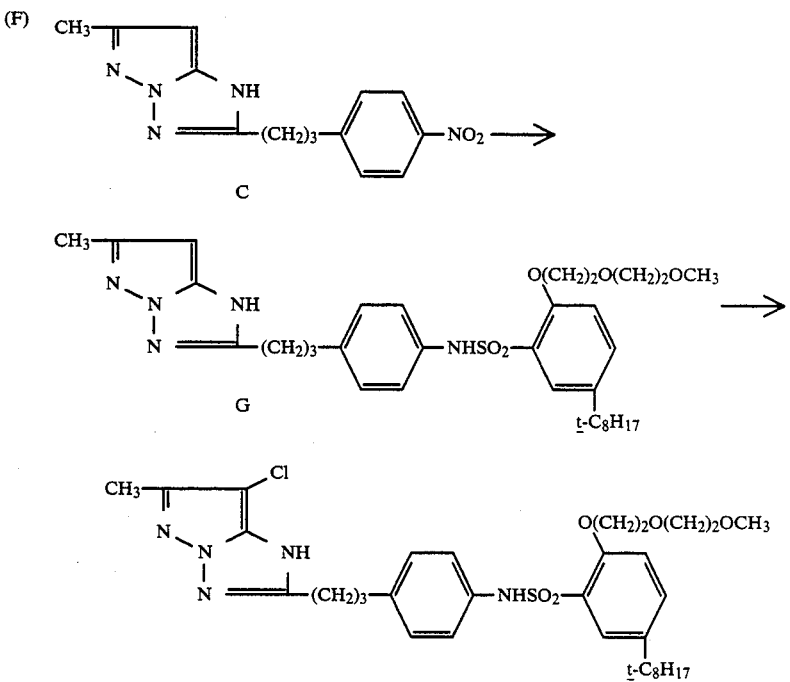

To a mixture of 100 ml of N,N-dimethylformamide and 150 ml of acetonitrile was added 23 g of 2-(3-(4-aminophenyl)propyl)-6-methyl-pyrazolo[1,5-b][1,2,4]triazole (Compound C) and the mixture was heated on a steam bath. To the mixture was added dropwise 41 g of 2-(2-(2-methoxyethoxy)ethoxy)-5-t-octyl-benzenesulfonyl chloride (Compound F) and the mixture was further stirred for 1.5 hours. The reaction mixture thus obtained was cooled, poured into water, and extracted with ethyl acetate. The organic solvent layer formed was collected, washed twice with water, dried on anhydrous sodium sulfate, concentrated, and then recrystallized from acetonitrile to provide 26 g (45%) of Compound G.

Then, 28.4 g of Compound G obtained above was dissolved in 250 ml of dichloromethane and after adding thereto 5.89 g of N-chlorosuccinic acid imide, the mixture was stirred for 10 minutes at room temperature. The reaction mixture thus obtained was washed twice with water, dried on anhydrous sodium sulfate, and then concentrated. The residue formed was recrystallized from acetonitrile to provide 26 g (86%) of Compound (22) as white crystals (m.p. 145°–146° C.).

Elemental Analysis:

|  | C | H | N |
|---|---|---|---|
| Calculated: | 60.03% | 7.02% | 10.61% |
| Found: | 60.01% | 6.94% | 10.52% |

The magenta couplers for use in this invention and other couplers which can be used together with the magenta couplers described hereinafter can be introduced into photographic light-sensitive materials by various dispersion methods, such as, for example, a solid dispersion method, an alkali dispersion method, preferably a latex dispersion method, and more preferably an oil drop-in-water dispersion method. In the oil drop-in-water dispersion method, the coupler is dissolved in a high-boiling organic solvent having a boiling point of higher than 175° C. and/or a low-boiling so-called auxiliary solvent and finely dispersed in a aqueous medium such as water and an aqueous gelatin solution in the presence of a surface active agent.

Examples of the high-boiling organic solvent are described in U.S. Pat. No. 2,322,027, etc., and will be illustrated hereafter. The dispersing procedure may be accompanied by phase transfer and if necessary, the auxiliary solvent may be removed or reduced by distillation, noodle washing, an ultrafiltration method, etc., before coating.

Specific examples of the high-boiling organic solvents are phthalic acid esters (e.g., dibutyl phthalate, di-3,7-dimethyloctyl phthalate, dicyclohexyl phthalate, di-2-ethylehexyl phthalate, didodecyl phthalate, etc.), phosphoric acid or phosphonic acid esters (e.g., triphenyl phosphate, tricresyl phosphate, 2-ethylhexyldiphenyl phosphate, tricyclohexyl phosphate, tri-2-ethylhexyl phosphate, tridecyl phosphate, tributoxyethyl phosphate, trichloropropyl phosphate, di-2-ethylhexylphenyl phosphate, etc.), benzoic acid esters (e.g., 2-ethylhexyl benzoate, dodecyl benzoate, 2-ethylhexyl-p-hydroxy benzoate, etc.), amides (e.g., diethyldodecanamide, N-tetradecylpyrrolidone, etc.), alcohols or phenols (e.g., isostearyl alcohol, 2,4-di-tert-amylphenol, etc.), aliphatic carboxylic acid esters (e.g., dioctyl azelate, glycerol tributyrate, isostearyl lactate, trioctyl citrate, etc.), anilines (e.g., N,N-dibutyl-2-butoxy-5-tert-octylaniline, etc.), hydrocarbons (e.g., paraffin, dodecylbenzene, diisopropylnaphthalene, etc.), etc.

Also, as the auxiliary solvents, organic solvents having boiling points of from about 30° C. to about 160° C. can be used. Specific examples are ethyl acetate, butyl acetate, ethyl propionate, methyl ethyl ketone, cyclohexanone, 2-ethoxyethyl acetate, dimethylformamide, etc.

Specific examples of the latex dispersion method, the effects thereof, and the latexes for impregnation are described in U.S. Pat. No. 4,199,363 etc.

The magenta couplers for use in this invention are preferably incorporated in light-sensitive silver halide emulsion layers. The addition amount thereof is from 0.003 to 9.5 mole, preferably from 0.005 to 0.3 mole per mole of silver halide for photography color photographic light-sensitive materials and is from 0.1 to 0.3 mole for color photographic papers.

The color photographic light-sensitive materials of this invention may further contain conventional couplers together with the above-described magenta couplers for use in this invention.

Typical examples of the useful color couplers are naphtholic or phenolic compounds, pyrazolone, or pyrazoloazole series compounds, and open chain or heterocyclic ketomethylene compounds. Cyan, magenta, and yellow couplers, which can be used in this invention, are described in the patents cited in *Research Disclosure*, No. 17643, Chapter VII (1978, December), ibid. No. 18717 (November, 1979).

It is preferred that these couplers have a ballast group or are polymerized non-diffusible couplers. Also, couplers providing colored dyes having appropriate diffusibility, colored couplers, non-coloring couplers, or couplers releasing a developing inhibitor or developing accelerator with the coupling reaction can be used in this invention.

Typical examples of the yellow couplers which can be used in this invention are oil protected type acylacetamide series couplers. Specific examples of the yellow couplers are described, for example, in U.S. Pat. Nos. 2,407,210, 2,875,057, and 3,265,506. In this invention, two-equivalent yellow couplers are preferably used and typical examples of such couplers are oxygen atom-releasing type yellow couplers described, for example, in U.S. Pat. Nos. 3,408,194, 3,447,928, 3,933,501, 4,401,752, etc., and nitrogen atom-releasing type yellow couplers described in, for example, Japanese Patent Publication No. 10,739/'83; U.S. Pat. Nos. 4,022,620, 4,326,024; *Research Disclosure*, No. 18053 (1979, April), U.K. Pat. No. 1,425,020; West German patent application (OLS) Nos. 2,219,917, 2,261,361, 2,329,587, and 2,433,812. α-pivaloylacetanilide series couplers yield of colored dyes of good fastness and α-benzoylacetanilide series couplers have a good coloring property.

Magenta couplers that can be used include oil protected type indazolo series or cyanoacetyl series couplers, and, preferably, pyrazoloazole series couplers such as 5-pyrazolone series couplers and pyrazolotriazole series couplers. A 5-pyrazolone series coupler substituted by an arylamino group or an acylamino group at the 3-position is preferred from the viewpoint of the hue and coloring speed of the colored dye. Typical examples of these couplers are described in U.S. Pat. Nos. 2,311,082, 2,343,703, 2,600,788, 2,908,573, 3,062,653, 3,152,896, 3,936,015, etc. Two-equivalent 5-pyrazolone series couplers are preferred in this invention and as the releasable group for the couplers, the nitrogen atom-releasing group described in U.S. Pat. No. 4,310,619 and the arylthio group described in U.S. Pat. No. 4,351,897 are preferred. Also, the 5-pyrazolone series couplers having the ballast groups described in European Pat. No. 73,636 show high coloring reactivity.

Cyan couplers which can be used in this invention include oil protected type naphtholic couplers and phenolic couplers. Specific examples of the naphtholic couplers are the naphtholic couplers described in U.S. Pat. No. 2,474,293 and the oxygen atom-releasing type high-active two-equivalent naphthol couplers described in U.S. Pat. Nos. 4,052,212, 4,146,396, 4,228,233, and 4,296,200. Specific examples of the phenolic couplers are described in U.S. Pat. Nos. 2,369,929, 2,423,730, 2,772,162, and 2,895,826.

Cyan couplers having fastness to heat, humidity, and light are preferably used in this invention, and typical examples of such cyan couplers are the phenolic cyan couplers described in U.S. Pat. No. 3,772,002, the 2,5-diacylamino-substituted phenolic cyan couplers described in U.S. Pat. Nos. 2,772,162, 3,758,308, 4,126,396, 4,334,011, and 4,327,173; West German patent application (OLS) No. 3,229,729; and Japanese patent application No. 42,761/'83; and the phenolic couplers having a phenylureido group at the 2-position and an acylamino group at the 5-position described in U.S. Pat. Nos. 3,446,622, 4,333,999, 4,451,559, 4,427,767, etc.

The couplers for use in this invention represented by formula (I) and the above-described couplers can be used in the same emulsion layer, as a combination of two or more kinds of the couplers, in order to satisfy the characteristics required for the photographic materials of this invention, or the same layers of the photographic material.

Moreover, in this invention, for correcting the undesired absorption of the colored dyes of the magenta coupler and the cyan coupler at a short wavelength region, it is preferred for color photographic materials to use colored couplers together with the above-described couplers. Typical examples of these colored couplers are the yellow-colored magenta couplers (i.e., yellow colored magenta dye-forming couplers) described in U.S. Pat. No. 4,163,670 and Japanese Patent Publication No. 39,413/'82, and the magenta-colored cyan couples described in U.S. Pat. Nos. 4,004,929, 4,138,258, and U.K. Pat. No. 1,146,368.

These color couplers may form dimers, oligomers or polymers. Typical examples of polymerized couplers are described in U.S. Pat. Nos. 3,451,820, 4,080,211, etc. Also, specific examples of polymerized magenta couplers are described in U.K. Pat. No. 2,102,173 and U.S. Pat. No. 4,367,282.

Also, couplers providing diffusible colored dyes can be used together with the foregoing couplers for improving graininess in this invention and specific examples of these couplers are magenta couplers described in U.S. Pat. No. 4,366,237 and U.K. Pat. No. 2,125,570 and yellow, magenta, and cyan couplers described in European Pat. No. 96,873 and West German patent application (OLS) No. 3,324,533.

As the binder or protective colloid for the silver halide emulsion layers, interlayers, etc., of the photographic materials of this invention, gelatin is advantageously used, but other hydrophilic colloids can be used individually or together with gelatin.

For the photographic emulsion layers of the photographic materials of this invention, silver bromide, silver iodobromide, silver iodochlorobromide, silver chlorobromide, or silver chloride may be used as the silver halide. A preferred silver halide is silver iodobromide containing less than 15 mole% silver iodide. A particularly preferred silver halide is silver iodobromide containing from 2 mole% to 12 mole% silver iodide.

There is no particular restriction on the mean grain size of the silver halide grains in the photographic emulsions (the mean grain size is the mean diameter of the grains when the silver halide grain is a spherical grain or a grain similar to spherical or is indicated as a mean value based on the projected areas by using an edge length as the grain size when the silver halide grain is a cubic grain).

The grain size distribution may be broad or narrow.

The silver halide grains in the photographic emulsions may have a regular form such as a cubic form or an octahedral form or may have an irregular crystal form such as a spherical form or a tabular form. Also, the silver halide grains may be a composite form of these crystal forms or may be composed of a mixture of silver halide grains having various crystal forms.

Also, a silver halide emulsion containing tabular silver halide grains having a diameter more than 5 times the thickness thereof which account for about 50% or more of the total projected areas of silver halide grains in the emulsion may be used in this invention.

The silver halide grains for use in this invention may have different phases between the inside thereof and the surface thereof. Also, the silver halide grains may be ones forming latent images mainly on the surfaces thereof or ones forming latent images mainly in the insides thereof.

The silver halide emulsions for use in this invention can be prepared by the methods described in, for example, P. Glafkides, *Chimie et Physique Photographique* (published by Paul Montel Co., 1967), G. F. Duffin, *Photographic Emulsion Chemistry* (published by The Focal Press, 1966), V. L. Zelikman et al, *Making and Coating Photographic Emulsion* (published by The Focal Press, 1964), etc. That is, the photographic emulsions may be prepared by an acid process, a neutralization process, an ammonia process, etc. Also, as the mode of reacting a soluble silver salt and a soluble halogen salt, a single jet method, a double jet method, or a combination thereof may be used.

A so-called back mixing method for forming silver halide grains in the presence of an excessive amount of silver ions can be used. As one mode of the double jet method, a so-called controlled double jet method of preparing a silver halide emulsion while maintaining the pAg in the liquid phase wherein the silver halide is formed at a constant value can be also used. According to this method, a silver halide emulsion containing silver halide grains having a regular crystal size and a substantially uniform grain size can be obtained.

Two or more silver halide emulsions separately prepared can be used as a mixture thereof.

The silver halide grains may be formed or physically ripened in the presence of a cadmium salt, a zinc salt, a lead salt, a thallium salt, an iridium salt or a complex salt thereof, a rhodium salt or a complex salt thereof, an iron salt or a complex salt thereof, etc.

The silver halide emulsions for use in this invention are usually chemically sensitized. The chemical sensitization can be performed using the methods described, for example, in H. Frieser edited, *Die Grundlagender Photographischen Prozesse mit Silberhalogeniden*, (Akademische Verlagsgessellschaft, 1968), pages 675–734.

For instance, there are a sulfur sensitization method using active gelatin or a sulfur-containing compound capable of reacting with silver (e.g., thiosulfates, thioureas, mercapto compounds, rhodanines, etc.); a reduction sensitization method using a reducing material (e.g., stannous salts, amines, hydrazine derivatives, formamidines, silane compounds, etc.); and a noble metal sensitization method using a noble metal compound (e.g., gold complex salts and complex salts of metals belonging to group VIII of the periodic table, such as Pt, Ir, Pd, etc.). They can be used individually or as a combination thereof.

The silver halide photographic emulsions for use in this invention may further contain various compounds for preventing the occurrence of fog during the production, storage, or photograhic processing of the photographic materials of this invention or for stabilizing the photographic properties. Examples of these compounds include azoles such as benzothiazolium salts, nitroimidazoles, nitrobenzimidazoles, chlorobenzimidazoles, bromobenzimidazoles, mercaptothiazoles, mercaptobenzothiazoles, mercaptobenzimidazoles, mercaptothiadiazoles, aminotriazoles, benzotriazoles, nitrobenzotriazoles, mercaptotetrazoles (in particular, 1-phenyl-5-mercaptotetrazole), etc.; mercaptopyrimidines, mercaptotriazines; thioketo compounds such as oxazolinethione; azaindenes such as triazaindenes, tetraazaindenes (in particular, 4-hydroxy-substituted (1,3,3a,7)tetraazaindenes), pentaazaindenes, etc.; benzenethiosulfonic acid; benzenesulfinic acid, benzenesulfonic acid amide, etc.

The silver halide photographic emulsion layers of the photographic materials of this invention may further contain polyalkylene oxide or derivatives thereof, such as the ethers, esters, amines, etc., thioether compounds, thiomorpholines, quaternary ammonium compounds, urethane derivatives, urea derivatives, imidazole derivatives, 3-pyrazolidones, etc., for the purpose of increasing sensitivity, increasing contrast, or accelerating development.

The photographic materials of this invention can contain dispersions of water-insoluble or sparingly water soluble synthetic polymers for improving the dimensional stability of the photographic emulsion layers and other synthetic colloid layers.

The silver halide emulsions for use in this invention may be spectrally sensitized by methine dyes, etc. The dyes which are used for this purpose include cyanine dyes, merocyanine dyes, complex cyanine dyes, complex merocyanine dyes, holopolar cyanine dyes, hemicyanine dyes, styryl dyes, and hemioxonole dyes. Particularly useful dyes are cyanine dyes, merocyanine dyes, and complex merocyanine dyes. In these dyes there can be used nuclei which are usually utilized for cyanine dyes as basic heterocyclic nuclei.

These sensitizing dyes may be used individually or as a combination thereof. A combination of sensitizing dyes is usually used for the purpose of super-sensitization.

The silver halide emulsions may further contain a dye which does not have a spectral sensitizing action by itself or a compound which does not substantially absorb visible light and shows super-sensitization together with the above-described sensitizing dye. Examples of such materials are aminostyryl compounds substituted by a nitrogen-containing heterocyclic group (described in, for example, U.S. Pat. Nos. 2,933,390 and 3,635,721), aromatic organic acid-formaldehyde condensation products (described in, for example, U.S. Pat. No. 3,743,510), cadmium salts, azaindene compounds, etc.

This invention can be applied to multilayer multicolor photographic material having on a support at least two silver halide emulsion layers each having different spectral sensitivity. A multilayer natural color photograhic material usually has on a support at least one red-sensitive emulsion layer, at least one green-sensitive emulsion layer, and at least one blue-sensitive emulsion layer. The disposition order of these emulsion layers may be optionally selected according to the desired purpose. The red-sensitive emulsion layer usually contains a cyan-forming coupler, the green-sensitive emulsion layer a magenta-forming coupler, and the blue-sensitive emulsion layer a yellow-forming coupler but other combinations may be employed if desired.

The photographic materials of this invention may further contain inorganic or organic hardening agents in the silver halide emulsion layers and other synthetic colloid layers. Examples of such hardening agent are active vinyl compounds (e.g., 1,3-triacryloyl-hexahydro-s-triazine, 1,3-vinylsulfonyl-2-propanol, etc.), active halogen compounds (e.g., 2,4-dichloro-6-hydroxy-s-triazine, etc.), mucohalogenic acids (e.g., mucochloric acid, mucophenoxychloric acid, etc.), etc. They can be used individually or as a combination thereof.

The photograhic materials of this invention may further contain color fogging prevention agents such as hydroquinone derivatives, aminophenol derivatives, etc.

The photographic materials of this invention may contain ultraviolet absorbents in the hydrophilic colloid layers. Examples of such ultraviolet absorbents are the aryl group-substituted benzotriazoles described in, for example, U.S. Pat. Nos. 3,533,794, 4,236,013; Japanese Patent Publication No. 6540/'76; and European Pat. No. 57,160, the butadienes described in U.S. Pat. Nos. 4,0450,229 and 4,195,999, the cinnamic acid esters described in U.S. Pat. Nos. 3,705,805 and 3,707,375, the benzophenones described in U.S. Pat. No. 3,215,530 and U.K. Pat. No. 1,321,355, and the macromolecular compounds having a ultraviolet absorbing group as described in U.S. Pat. Nos. 3,761,272 and 4,431,726. Ultraviolet absorbing optical whitening agents as described in U.S. Pat. Nos. 3,499,762, 3,700,455, etc. may be used. Typical examples of ultraviolet absorbents are described, for example, in *Research Disclosure* No. 24239 (1984, June), etc.

The photographic materials of this invention may further contain water-soluble dyes as filter dyes or for irradiation prevention and various other purposes in the hydrophilic colloid layers. Examples of such dyes are oxonol dyes, hemioxonol dyes, styryl dyes, merocyanine dyes, cyanine dyes, and azo dyes. As these dyes, oxonol dyes, hemioxonol dyes, and merocyanine dyes are especially useful.

In the practice of this invention, fading preventing agents or dye image stabilizers may also be used together with the above-described couplers. The dye image stabilizers may be used singly or as a mixture thereof. Examples of the fading preventing agents are hydroquinone derivatives, gallic acid derivatives, p-alkoxyphenols, p-oxyphenol derivatives, bisphenols, etc.

The photographic material of this invention is prepared by coating silver halide emulsions for forming dye image-forming layers on a flexible support usually used for photographic materials, such as a plastic film, a paper, a cloth, etc.

Examples of the useful flexible support are films composed of a semisynthetic or synthetic polymer such as cellulose acetate, cellulose acetate butyrate, polystyrene, polyethylene terephthalate, polycarbonate, etc.; and papers coated or laminated with a baryta layer or α-olefin polymer (e.g., polyethylene, polypropylene, etc.). The support may be colored by using a dye or pigment or may be colored in black for the purpose of light shielding.

When the support is used for reflection type photographic materials, it is preferred to add a white pigment.

Examples of the white pigment are titanium dioxide, barium sulfate, zinc oxide, zinc sulfide, calcium carbonate, antimony trioxide, silica white, alumina white, titanium phosphate, etc. Of these pigments, titanium dioxide, barium sulfate, zinc oxide, etc., are particularly advantageous.

A subbing treatment is generally applied to the surface of the support for improving the adhesion for photographic emulsion layers, etc. Furthermore, the surface of the support may be subjected to corona discharging, ultraviolet irradiation, flame treatment, etc., before and/or after the subbing treatment.

Also, in the case of reflective type photographic materials, a hydrophilic colloid layer containing a white pigment at a high concentration can be formed between the support and the silver halide emulsion layer for improving the whiteness and the sharpness of the photographic images.

In reflective type photographic materials containing the magenta couplers of this invention, polymer-laminated paper supports are frequently used as the support, but a synthetic resin film kneaded with a white pigment can also be used as the support. In the latter case, the photographic material is excellent in flatness, luster, and sharpness, and photographic images particularly excellent in saturation and regeneration of dark portions are obtained. In this case, as the synthetic resin film, polyethylene terephthalate, cellulose acetate, etc., are preferably used and as the white pigment, barium sulfate, titanium oxide, etc., are particularly preferred.

The color photographic materials of this invention may further contain various other additives known in the art, such as stabilizers, antifoggants, surface active agents, antistatic agents, developing agents, etc., and specific examples of these additives are described in *Research Disclosure*, No. 17643 (December, 1978).

Furthermore, as the case may be, the photographic materials of this invention may contain, in the silver halide emulsion layers or synthetic colloid layers, a fine grain silver halide emulsion having substantially no light sensitivity (e.g., an silver chloride, silver bromide, or silver chlorobromide emulsion having a mean grain size of less than 0.20 μm).

A color developer for processing the color photographic materials of this invention is an alkaline aqueous solution containing, preferably, an aromatic primary amine color developing agent as the main component. Examples of the color developing agent are 4-amino-N,N-diethylaniline, 3-methyl-4-amino-N,N-diethylaniline, 4-amino-N-ethyl-N-β-hydroxyethylaniline, 3-methyl-4-amino-N-ethyl-N-β-hydroxyethylaniline, 3-methyl-4-amino-N-ethyl-N-β-methanesulfoamidoethylaniline, 4-amino-3-methyl-N-ethyl-N-β-methoxyethylaniline, etc.

The color developer may contain a development inhibitor or antifoggant such as a bromide, an iodide, and an organic antifoggants, or a pH buffer such as the sulfites, carbonates, borates, and phosphates of alkali metals. Also, the color developers may contain, if necessary, water softeners; preservatives such as hydroxylamine, etc.; organic solvents such as benzyl alcohol, diethylene glycol, etc.; development accelerators such as polyethylene glycol, quaternary ammonium salts, amines, etc.; dye-forming couplers; competing couplers; fogging agents such as sodium borohydride, etc.; auxiliary developing agents such as 1-phenyl-3-pyrazolidone, etc.; tackifiers; the polycarboxylic acid chelating agents described, for example, in U.S. Pat. No. 4,083,723; the antioxidants described in West German patent application (OLS) No. 2,622,950, etc.

The color photographic materials of this invention are usually bleached after color development. The bleach process may be performed simultaneously with or separately from a fix process. Examples of the bleaching agent are compounds of multivalent metals such as iron(III), cobalt(III) chromium(VI), copper(II), etc., peracids, quinones, nitroso compounds, etc. Specific examples of the bleaching agent are ferricyanides, dichromates, organic complex salts of iron(III) or cobalt(III); aminopolycarboxylic acids such as ethylenediaminetetraacetic acid, nitrilotriacetic acid, 1,3-diamino-2-propanoltetraacetic acid, etc.; complex salts of organic acid such as citric acid, tartaric acid, malic acid, etc.; persulfates; manganates; nitrosophenol, etc.

In these materials, potassium ferricyanide, ethylenediaminetetraacetic acid iron(III) sodium and ethylenediaminetetraacetic acid iron(III) ammonium are particularly useful. The ethylenediaminetetraacetic acid iron(III) complex salts are useful in both the bleach solution and the mono-bath bleach solution (blix solution).

The photographic materials may be washed with water after a color development and/or bleach and fix processes or a blix process.

The color development can be performed at temperatures between 18° C. and 55° C. The color development is preferably performed at temperatures above 30° C., in particular above 35° C. The developing time can be in a range of about 1 min. to about 3.5 min., but is generally made as short as practically possible.

For continuous processing of color photographic materials, a supplement of the development liquid is preferred, and a fresh developer is usually supplemented in an amount of from 160 ml to 330 ml, preferably less than 100 ml, per square meter of the processing area. When benzyl alcohol is used for a color developer, the content thereof is preferably less than 5 ml/liter.

The blix process can be practiced at 18° C. to 50° C., preferably above 35° C. When the blix is performed above 35° C., the processing time can be reduced to less than 1 min. as well as the supplemental amount of the processing liquid can be reduced.

The time required for washing applied after color development or bleach and fix or blix is usually within 3 minutes and can be reduced within one minute by using a stabilization bath.

Colored dyes are generally deteriorated by the action of light, heat, and humidity, as well as being faded by fungi. The deterioration of cyan dye images by fungi is particularly a problem, and it is preferred to use an antifungal agent. Examples of antifungal agents are the 2-thiazolylbenzimidazoles described in Japanese patent application (OPI) No. 157,244/'82. The antifungal agent may be incorporated in the photographic materials or may be added from outside the development process. The addition of the antifungal agent may be performed in any step provided that the agent is in the photographic materials after processing.

The invention will now be explained practically by referring to the following examples but the invention is not limited to these examples.

Unless otherwise stated, all percents, ratios, etc., are by weight.

EXAMPLE 1

In 19.3 ml of tri(2-ethylhexyl) phosphate and 25 ml of ethyl acetate was dissolved 9.6 g of Compound (1)

shown above under heating. Then, the coupler solution thus formed was added to 100 ml of an aqueous solution containing 10 g of gelatin and 1.0 g of sodium dodecylbenzenesulfonate with stirring at high speed to provide a finely emulsified dispersion of the coupler solution. The total amount of the emulsified dispersion was added to 100 g of a silver chlorobromide emulsion (containing 6.5 g of silver) containing 50 mole% bromine and after adding thereto 10 ml of a solution of 2% 2,4-dichloro-6-hydroxy-s-triazine sodium salt as a hardening agent, the resultant mixture was coated on a paper support having a polyethylene layer laminated on both surfaces at a silver coverage of 200 mg/m² and further a gelatin layer was coated on the emulsion layer to provide Sample A.

Then, Compound (1) was replaced by 8.3 g of Compound (8), 9.7 g of Compond (22), 8.3 g of Compound (32), 8.1 g of Compound (34), 8.8 g of Compound (57), and 8.3 g of Compound (58), respectively, and to each compound was added tri(2-ethylhexyl) phosphate in an amount of 16.5 ml, 19.5 ml, 16.5 ml, 16.0 ml, 17.5 ml, and 16.5 ml, respectively. Further, 25 ml of ethyl acetate was added to each of the mixtures, whereby emulsified dispersions were prepared in the same procedure as above. Each of the dispersions was added to the same amount of the silver halide emulsion as above, and the resulting mixture was coated on a support as used above at the same silver coverage. Thus, Samples B, C, D, E, F, and G were prepared.

Furthermore, for comparison, to each of the following Comparison Compound (1) (8.9 g) and Comparison Compound (2) (10.3 g) was added tri(2-ethylhexyl) phosphate in an amount of 17.8 ml and 20.6 ml, respectively, and 25 ml of ethyl acetate was added to each of the mixtures, whereby Comparison Samples 1 and 2 were prepared in the same procedure as above.

Comparison Compound (1):

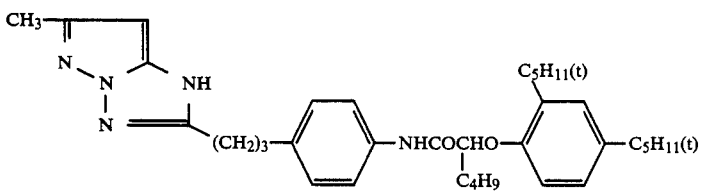

Comparison Compound (2):

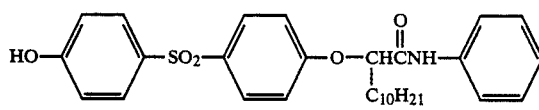 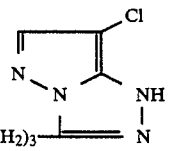

Each of the Samples thus prepared was wedge exposed at 1000 C.M.S. and then processed by the following steps.

| Processing step | Temperature | Time |
| --- | --- | --- |
| Development | 33° C. | 3 min. 30 sec. |
| Blix | 33° C. | 1 min. 30 sec. |
| Wash | 28–35° C. | 3 min. |

The compositions of the processing solutions used above were as follows.

Developer

| | |
| --- | --- |
| Benzyl Alcohol | 15 ml |
| Diethylenetriaminepentaacetic acid | 5 g |
| Potassium Bromide | 0.4 g |
| Na$_2$SO$_3$ | 5 g |
| Na$_2$CO$_3$ | 30 g |
| Hydroxylamine Sulfate | 2 g |
| 4-Amino-3-methyl-N—β-(methanesulfonamido)ethylaniline.3/2H$_2$SO$_4$.H$_2$O | 4.5 g |
| Water to make | 1000 ml |
| pH 10.1 | |

Blix Solution

| | |
| --- | --- |
| Ammonium Thiosulfate (70 wt %) | 150 ml |
| Na$_2$SO$_3$ | 5 g |
| Na[Fe(EDTA)] | 40 g |
| EDTA | 4 g |
| Water to make | 1000 ml |
| pH 6.8 | |

The magenta dye images of each sample thus obtained were color image having good hue and high saturation. The photographic characteristics of these color images were measured and the results obtained are shown in Table 1.

TABLE 1

| Sample | Relative Sensitivity* | Gradation | Maximum Density |
| --- | --- | --- | --- |
| Comparison Sample 1 | 100 | 2.90 | 2.73 |
| Comparison Sample 2 | 105 | 2.94 | 2.97 |
| Sample A | 92 | 3.17 | 3.15 |
| Sample B | 89 | 3.35 | 3.15 |
| Sample C | 86 | 3.22 | 3.17 |
| Sample D | 88 | 3.35 | 3.05 |
| Sample E | 96 | 3.16 | 2.86 |
| Sample F | 92 | 3.28 | 3.02 |
| Sample G | 98 | 3.19 | 2.91 |

*Relative value of the exposure amount so as to give a density of fog +0.5. The relative sensitivity of the comparison sample was defined as 100.

From the results shown above, it can be seen that the magenta couplers for use in this invention show excellent photographic characteristics in sensitivity, gradation, and maximum density. This is considered to be due to the fact that the coupling activity and coloring efficiency are increased by the introduction of a sulfonamido group.

EXAMPLE 2

Each of Samples H, I, J, K, L, and M of color photographic light-sensitive materials was prepared by coating Layer 1 (lowermost layer) to Layer 7 (uppermost layer) shown below, in succession, on a paper support having a polyethylene layer on both surfaces.

In this case, the emulsified dispersion containing magenta coupler and the coating composition containing the emulsified dispersion and a silver halide emulsion used for each Layer 3 were prepared in the same manner as in Example 1.

Layer 1: A layer containing a blue-sensitive silver chlorobromide emulsion (80 mol% Br, silver coverage of 350 mg/m$^2$), 1500 mg/m$^2$ of gelatin, 500 mg/m$^2$ of a yellow coupler*1, and 400 mg/m$^2$ of a solvent*2.

Layer 2: A layer containing 1100 mg/m$^2$ of gelatin, 200 mg/m$^2$ of a color mixing preventing agent*3, and 100 mg/m$^2$ of a solvent*4.

Layer 3: A layer containing a green-sensitive silver chlorobromide emulsion (50 mol% Br, silver coverage of 180 mg/m$^2$), $3.4 \times 10^{-4}$ mol/m$^2$ of a magenta coupler*5, and a solvent*6 in a coverage two times more than the corresponding coverage of the magenta coupler.

Layer 4: A layer containing 1600 mg/m$^2$ of gelatin, 700 mg/m$^2$ of a ultraviolet absorbent*7, 200 mg/m$^2$ of a color mixing preventing agent*3, and 300 mg/m$^2$ of a solvent*4.

Layer 5: A layer containing a red-sensitive silver chlorobromide emulsion (50 mol% Br, silver coverage of 300 mg/m$^2$, 1200 mg/m$^2$ of gelatin, 400 mg/m$^2$ of a cyan coupler*8, and 250 mg/m$^2$ of a solvent*4.

Layer 6: A layer containing 1000 mg/m$^2$ of gelatin, 360 mg/m$^2$ of an ultraviolet absorbent*7, and 120 mg/$^2$ of a solvent*4.

Layer 7: A layer containing 1600 mg/m$^2$ of gelatin.

The compounds used for the above layers were as follows.

*1: Yellow coupler: α-Pivaloyl-α-(2,4-dioxo-5,5'-dimethyloxazolidin-3-yl)-2-chloro-5-[α-(2,4-di-tert-pentylphenoxy)butanamido]acetanilide.
*2: Solvent: Dioctylbutyl phosphate.
*3: color mixing preventing agent: 2,5-Dioctylhydroquinone.
*4: Solvent: Dibutyl phthalate.
*5: Magenta coupler: Compound (1) for Sample H, Compound (8) for Sample I, Compound (22) for Sample J, Compound (32) for Sample K, Compound (34) for Sample L, and Comparison Compound (1) as shown in Example 1 for Sample M.
*6: Solvent: Tri(2-ethylhexyl) phthalate.
*7: Ultraviolet absorbent: 2-(2-Hydroxy-3-sec-butyl-5-tert-butylphenyl) benzotriazole.
*8: Cyan coupler: 2-[α-2,4-Di-tert-pentylphenoxy)-butanamido]-4,6-dichloro-5-methylphenol.

Each of these samples was exposed as in Example 1, using trichromatic separtion filters of blue, green and red, and then processed.

The photographic properties thus obtained are shown in Table 2 below.

TABLE 2

| Sample | Relative Sensitivity* | Gradation | Maximum Density |
|---|---|---|---|
| Comparison Sample M | 100 | 2.88 | 2.95 |
| Sample H | 91 | 3.14 | 3.14 |
| Sample I | 88 | 3.33 | 3.15 |
| Sample J | 84 | 3.21 | 3.17 |
| Sample K | 90 | 3.21 | 3.15 |
| Sample L | 95 | 3.08 | 2.93 |

*Relative value of the exposure amount giving a density of fog +0.5. The relative sensitivity of the comparison sample was defined as 100.

From these results, it can be seen that the couplers for use in this invention also give excellent photographic characteristics in multilayer samples.

EXAMPLE 3

By following the same procedure as the cases of preparing Samples H, I, J, K, L, and M in Example 2 except that each emulsified dispersion containing the magenta coupler for each Layer 3 further containing the light-fading preventing agent shown below was used, Samples N, O, P, Q, R, and S were prepared.

Light fading preventing agent:

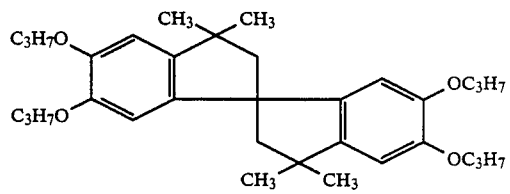

Each of Samples H to M prepared in Example 2 and Samples N to S prepared above was exposed as in Example 1 using trichromatic separation filters of blue, green, and red and processed as in Example 1 to provide colored images. These colored images were exposed using a fluorescent lamp fade-o-meter (15,000 lux) for 4 weeks and the light fastness test of magenta dye images was performed. The results obtained are shown in Table 3.

TABLE 3

| Sample | Density Change |
|---|---|
| Sample M (Comparison Compound (1)) | 0.63 |
| Sample H (Compound (1)) | 0.67 |
| Sample I (Compound (8)) | 0.64 |
| Sample J (Compound (22)) | 0.68 |
| Sample K (Compound (32)) | 0.65 |
| Sample L (Compound (34)) | 0.64 |
| Sample S (Comparison Compound (1) + F.P.A.) | 0.91 |
| Sample N (Compound (1) + F.P.A.) | 0.95 |
| Sample O (Compound (8) + F.P.A.) | 0.93 |
| Sample P (Compound (22) + F.P.A.) | 0.96 |
| Sample Q (Compound (32) + F.P.A.) | 0.93 |
| Sample R (Compound (34) + F.P.A.) | 0.93 |

F.P.A.: Light-fading preventing agent. The numeric value shown in the table is the magenta density value after the fading test of the portion having the initial density of 1.0.

From the results shown above, it can be seen that the couplers having a sulfonamido group according to this invention are excellent in light fastness of colored imgages and fastness thereof can be improved by using a light fading preventing agent.

In addition, it was confirmed that the couplers for use in this invention had excellent properties of almost not causing fading of the colored images thereof by a color image fastness test under a high temperature of 100° C. and under high-temperature high-humidity conditions of 60° C. and 90% RH, and giving no stains of uncolored portions by remaining couplers after processing.

While the invention has been described in detail and with reference to specific embodiments thereof, it will be apparent to one skilled in the art that various changes and modifications can be made therein without departing from the spirit and scope thereof.

What is claimed is:

1. A silver halide color photographic material comprising a support having formed thereon at least one silver halide emulsion layer containing a pyrazoloazole series magenta coupler having a group expressed by the following general formula [S] at a position other than the coupling active position $$-(A)_n-L-B \qquad [S]$$

wherein A represents a substituted or unsubstituted alkylene group where the substituent is selected from the group consisting of an alkyl group, an aryl group, a halogen atom, a carbonamido group, a sulfonamido group and an alkoxy group, a substituted or unsubstituted cycloalkylene group where the substituent is selected from the group consisting of an aryl group and a halogen atom, a substituted or unsubstituted arylene group where the substituent is selected from the group consisting of a halogen atom and a carbonamido group, or a substituted or unsubstituted aralkylene group where the substituent is selected from the group consisting of a halogen atom and an alkyl group, in which in the main chain of said alkylene group, cycloalkylene group, arylene group, or aralkylene group —O—, —S—, —CO—, —CO$_2$—, —OCO—, $$\overset{R}{-\underset{|}{N}CO-},\ \overset{R}{-\underset{|}{N}-},\ \overset{R}{-\underset{|}{C}ON-},\ \overset{R}{-\underset{|}{N}CO_2-},$$

$$\overset{R}{-\underset{|}{O}CON-},\ \text{or}\ \overset{R}{-\underset{|}{N}}\overset{R'}{\underset{|}{C}ON-}$$

may be contained; L represents $$\overset{R}{-\underset{|}{N}SO_2-},\ -\overset{R}{\underset{|}{S}O_2N-},\ \text{or}\ \overset{R}{-\underset{|}{N}}\overset{R'}{\underset{|}{S}O_2N-};$$

B represents a hydrogen atom or a substituted or unsubstituted alkyl or aryl group which does not contain therein —SO$_2$—, n is 0 or 1; R and R' each represents a hydrogen atom, a substituted or unsubstituted alkyl group, or a substituted or unsubstituted aryl group, provided that in the case that said pyrazoloazole series magenta coupler is a 1H-pyrazolo[5,1-c][1,2,4]triazole derivative, A does not represent an aralkylene group containing an arylene group directly connected to L, wherein said pyrazoloazole series magenta coupler is a compound represented by the following general formula (I-1), (I-2), (I-3), (I-4), (I-5) or (I-6):

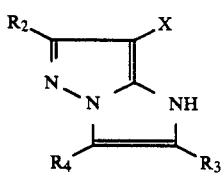

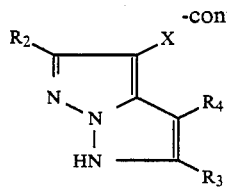

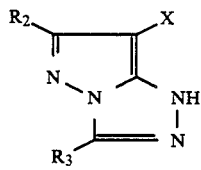

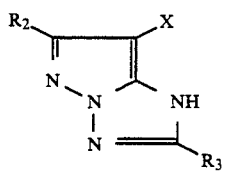

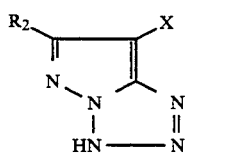

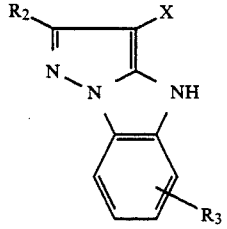

wherein R$_2$, R$_3$ and R$_4$ each represents a hydrogen atom, a halogen atom, an alkyl group, an aryl group, a heterocyclic group, a cyano group, an alkoxy group, an aryloxy group, a heterocyclic oxy group, an acyloxy group, a carbamoyloxy group, a silyloxy group, a sulfonyloxy group, an acylamino group, an anilino group, a ureido group, an imido group, a sulfamoylamino group, a carbamoylamino group, an alkylthio group, an arylthio group, a heterocyclic thio group, an alkoxycarbonylamino group, an aryloxycarbonylamino group, a sulfonamido group, a carbamoyl group, an acyl group, a sulfamoyl group, a sulfonyl group, a sulfinyl group, an alkoxycarbonyl group, or an aryloxycarbonyl group, in which at least one of R$_2$, R$_3$ and R$_4$ represents said group expressed by the general formula [S]; and X represents a hydrogen atom or a group bonded to a carbon atoms at the coupling position through an oxygen atom, a nitrogen atom or a sulfur atom and wherein said group expressed by the general formula [S] is a group expressed by the following general formula [S-1]

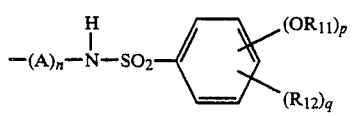

wherein A and n each has the same meaning as defined above; R$_{11}$ represents a hydrogen atom, an alkyl group, a cycloalkyl group, an aryl group, an aralkyl group, or an acyl group; $R_{12}$ is selected from the group consisting of an alkoxy group, an alkyl group and a halogen atom; p represents an integer of from 1 to 5; q represents an integer of from 0 to 4; and p+q is an integer of from 1 to 5.

2. A silver halide color photographic material as claimed in claim 1, wherein said group expressed by the general formula [S] is a group expressed by the following general formula [S-2] or [S-3]

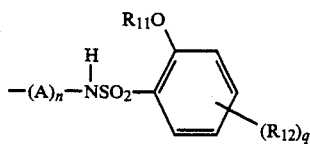

[S-2]

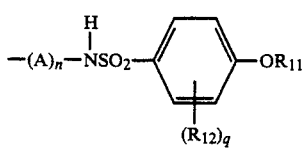

[S-3]

wherein A and n each has the same meaning as defined in claim 1; $R_{11}$ represents a hydrogen atom, an alkyl group, a cycloalkyl group, an aryl group, an aralkyl group, or an acyl group; $R_{12}$ has the same meaning as in claim 1; and q represents an integer of from 0 to 4.

3. A silver halide color photographic material as claimed in claim 1, wherein said pyrazoloazole series magenta coupler is a compound expressed by the following general formula (I-3)

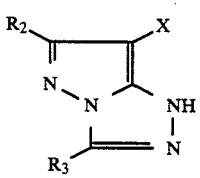

(I-3)

wherein $R_2$ and $R_3$ each represents a hydrogen atom, a halogen atom, an alkyl group, an aryl group, a heterocyclic group, a cyano group, an alkoxy group, an aryloxy group, a heterocyclic oxy group, an acyloxy group, a carbamoyloxy group, a silyloxy group, a sulfonyloxy group, an acylamino group, an anilino group, a ureido group, an imido group, a sulfamoylamino group, a carbamoylamino group, an alkylthio group, an arylthio group, a heterocyclic thio group, an alkoxycarbonylamino group, an aryloxycarbonylamino group, a sulfonamido group, a carbamoyl group, an acyl group, a sulfamoyl group, a sulfonyl group, a sulfinyl group, an alkoxycarbonyl group, or an aryloxycarbonyl group, in which at least one of $R_2$ and $R_3$ represents said group expressed by the general formula [S]; and X represents a hydrogen atom or a group bonded to a carbon atom at the coupling position through an oxygen atom, a nitrogen atom or a sulfur atom, and said group expressed by the general formula [S] is a group expressed by the following general formula [S-2]

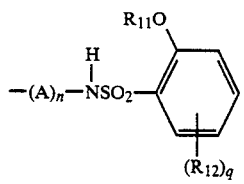

[S-2]

wherein A and n are defined hereinbefore; $R_{11}$ represents a hydrogen atom, an alkyl group, a cycloalkyl group, an aryl group, an aralkyl group, or an acyl group; $R_{12}$ has the same meaning as in claim 1 and q represents an integer of from 0 to 4.

4. A silver halide color photographic material as claimed in claim 2, wherein $R_{11}$ represents an alkyl group.

5. A silver halide color photographic material as claimed in claim 1, wherein said pyrazoloazole series magenta coupler is a compound represented by the general formula (I-1) or (I-4).

6. A silver halide color photographic material as claimed in claim 1, wherein said pyrazoloazole series magenta coupler is a compound represented by the general formula (I-4).

7. A silver halide color photographic material as claimed in claim 6, wherein in the general formula [S], n is 1.

8. A silver halide color photographic material as claimed in claim 3, wherein in the general formula [S-2], n is 1.

* * * * *